United States Patent [19]

Kurono et al.

[11] 4,045,468
[45] Aug. 30, 1977

[54] 16-CYCLOBUTYL-PROSTAGLANDINS

[75] Inventors: Masayasu Kurono, Osaka; Hisao Nakai; Takashi Muryobayashi, both of Ibaragi, all of Japan

[73] Assignee: Ono Pharmaceutical Company, Osaka, Japan

[21] Appl. No.: 557,437

[22] Filed: Mar. 11, 1975

[30] Foreign Application Priority Data

Mar. 14, 1974 Japan .................... 49-28544

[51] Int. Cl.$^2$ .......................... C07C 177/00
[52] U.S. Cl. ................. 260/468 D; 260/343.3 R; 260/345.7 P; 260/468 H; 260/473 A; 260/514 D; 260/521 B; 260/544 Y; 260/946; 260/346.22; 542/426; 424/305; 424/308; 424/317
[58] Field of Search ........... 260/514 D, 468 D, 69, 260/473, 520

[56] References Cited
FOREIGN PATENT DOCUMENTS 782,822  4/1971  Belgium ................... 260/468
807,046  11/1972  Belgium ................... 260/468

Primary Examiner—Robert Gerstl
Attorney, Agent, or Firm—Albert H. Graddis; Frank S. Chow

[57] ABSTRACT

Prostaglandin analogues of the formula:

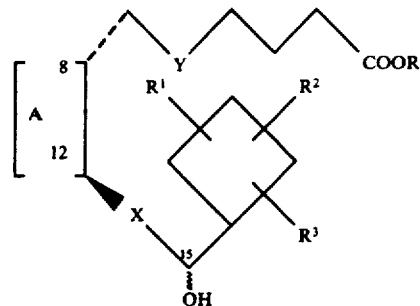

wherein A represents a grouping of the formula:

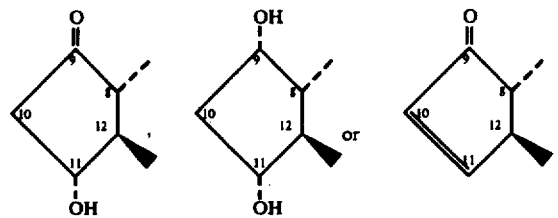

X represents trans-vinylene or ethylene and Y represents cis-vinylene or ethylene, R represents hydrogen or alkyl of 1 through 12 carbon atoms, $R^1$, $R^2$ and $R^3$ represent hydrogen, or alkyl of 1 through 12 carbon atoms or an aryl group, with the proviso that at least one of the symbols $R^1$, $R^2$ and $R^3$ represents an alkyl or aryl group, are new compounds possessing useful pharmacological properties; they are especially useful for the treatment of gastric ulceration.

9 Claims, No Drawings

16-CYCLOBUTYL-PROSTAGLANDINS

This invention is concerned with new prostaglandin analogues.

Prostaglandins are derivatives of prostanoic acid which has the following formula:

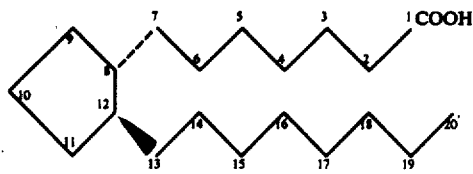

I

Various types of prostaglandins are known, the types depending inter alia on the structure and substituents on the alicyclic ring. For example, the alicyclic rings of prostaglandins E(PGE), and A(PGA) have the structures:

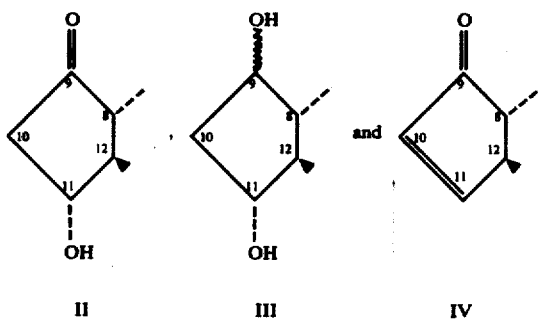

II   III   IV respectively. The dotted lines in the foregoing formulae and in other formulae throughout this specification denote, in accordance with generally accepted rules of nomenclature, that the attached grouping lies behind the general plane of the ring system, i.e. that the grouping is in α-configuration, that the thickened lines ◄ denote that the grouping lies in front of the general plane of the system, i.e. that the grouping is in β-configuration, and that the wavy line ∼ indicates that the grouping is in α- or β- configuration.

Such compounds are sub-classified according to the position of double bond(s) in the side chain(s) attached to the 8- and 12-positions of the alicyclic ring. Thus $PG_1$ compounds have a trans-double bond between $C_{13}-C_{14}$(trans-$\Delta^{13}$) and $PG_2$ compounds have a cis-double bond between $C_5-C_6$ and a trans-double bond between $C_{13}-C_{14}$(cis-$\Delta^5$, trans-$\Delta^{13}$). For example, prostaglandin $F_{1\alpha}$ ($PGF_{1\alpha}$) and prostaglandin $E_1$ ($PGE_1$) are characterized by the following structures V and VI.

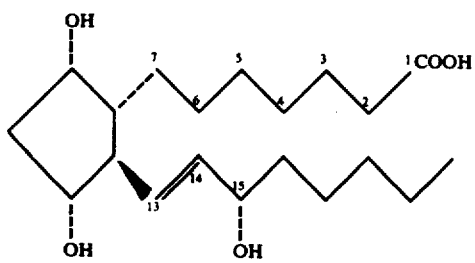

V

VI

-continued

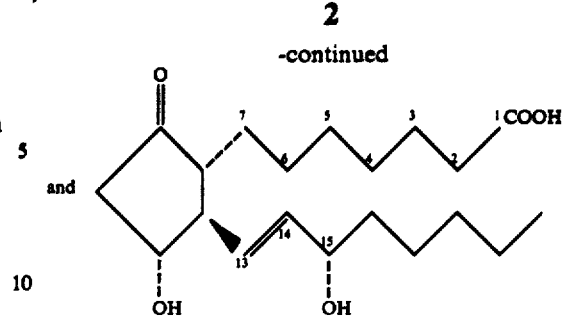

respectively. The structures of $PGF_{2\alpha}$ and $PGE_2$, as members of the $PG_2$ group, correspond to those of formulae V and VI respectively with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin-$F_{1\alpha}$ (dihydro-$PGF_{1\alpha}$) and dihydro-prostaglandin-$E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomemclature, as ω-homo-prostaglandins (methylene group added) or ω-nor-prostaglandins (methylene group eliminated), and, when more than one methylene group is added or eliminated, the number is indicated by di-, tri- etc. before the prefix "homo" or "nor."

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's and PGA's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGE's and PGF's have a stimulating effect on smooth muscle and increase the intestinal peristalsis; these actions indicate therpeutic utility on post-operative ileus and as purgatives. Furthermore, PGE's and PGF's may be used as oxytocics, as abortifacients in the first and second trimesters; in the post-labour abortion of the placenta, and as oral contraceptives because they regulate the sexual cycle of the female mammals. PGE's and PGA's have vasodilator and diuretic activities. PGE's are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties or the 'natural' prostaglandins or one or more of such properties to an enhanced degree, or hitherto unknown pharmacological properties. It has now been found after research and experimentation that by introducing a substituted cyclobutyl radical on the carbon atom in the 15-position of prostaglandins E, F and A and certain analogues thereof, the pharmacological properties of the 'natural' prostaglandins may, in some aspects of their activities, be improved or modified.

The present invention accordingly provides the new prostaglandin analogues of the general formula:

VII

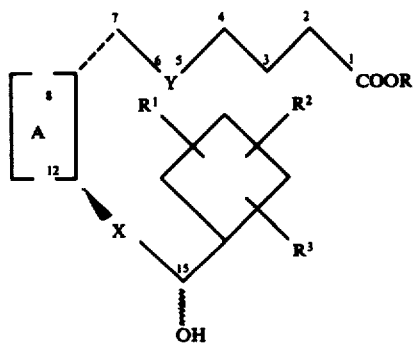

[wherein A represents a grouping of formula II or IV as indicated hereinbefore or a grouping of the formula:

IIIA

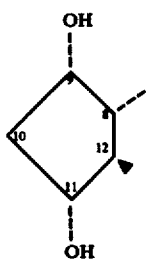

, X represents trans-vinylene (i.e. —CH=CH—) or ethylene (i.e. —CH$_2$CH$_2$—) and Y represents cis-vinylene or ethylene, R represents a hydrogen atom or a straight- or branched-chain alkyl group containing from 1 to 12 carbon atoms (preferably methyl), R$^1$, R$^2$ and R$^3$, which may be the same or different, each represent a hydrogen atom or a straight- or branched-chain alkyl group containing from 1 to 12 (preferably 1 to 6) carbon atoms or an unsubstituted or substituted aryl (preferably phenyl) group with the proviso that at least one of the symbols R$^1$, R$^2$ and R$^3$ represents an alkyl or unsubstituted or substituted aryl group] and cyclodextrin clathrates of such acids and esters, and, when R represents a hydrogen atom, non-toxic (e.g. sodium) salts thereof. Preferably the hydroxy group attached to the C-15 carbon atom of formula VII is an α-configuration.

The substituted aryl groups within the definition of symbols R$^1$, R$^2$ and R$^3$ may carry one, two or three substituents selected from alkyl, alkoxy, alkylthio, monoalkylamino and dialkylamino groups and halogen atoms, the alkyl groups or moieties of the said groups containing from 1 to 5 carbon atoms in a straight- or branched-chain.

The present invention is concerned with all compounds of general formula VII in the 'natural' form or its enantiomeric form, or mixtures thereof, more particularly the racemic form consisting of equimolecular mixtures of natural and its enantiomeric form.

As will be apparent to those skill in the art, the compounds depicted in general formula VII have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carries a hydroxy group on the carbon atom in position 11 (i.e. when the ring is that of formula II) or hydroxy groups in positions 9 and 11 (i.e. when the ring is that of formula IIIA) and further centres of chirality may occur when at least one of the symbols R$^1$, R$^2$ and R$^3$ represents a branched-chain alkyl group. The presence of chirality leads, as is well known, to the existence of isomerism. However, the compounds of general formula VII all have such a configuration that the sidechains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans-configuration and have a hydroxy group as depicted in the 15-position are to be considered within the scope of formula VII.

According to a feature of the present invention, the prostaglandin analogues of general formula VII, wherein R represents a hydrogen atom and the other symbols are as hereinbefore defined, are prepared by the process which comprises the hydrolysis to hydroxy groups of the groups —OR$^4$ of a cyclopentane derivative of the general formula:

VIII

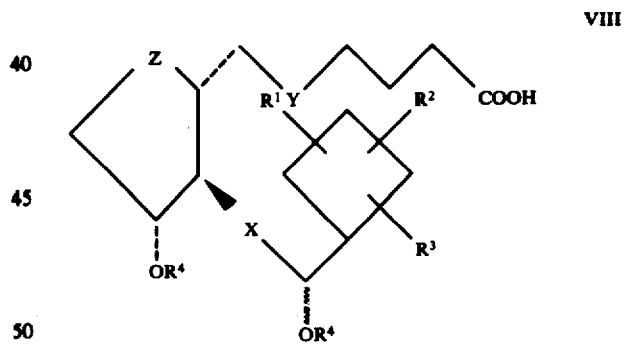

(wherein X, Y, R$^1$, R$^2$ and R$^3$ are as hereinbefore defined, Z represents

or C=O, and R$^4$ represents a 2-tetrahydrofuranyl group, a 1-ethoxyethyl group or, preferbly, 2 -tetrahydropyranyl group unsubstituted or substituted by at least one alkyl group) to obtain a prostaglandin analogue of the general formula:

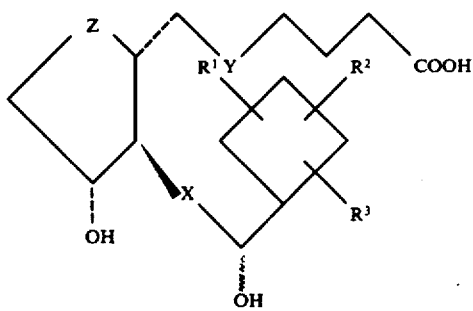

IX (wherein the various symbols are as hereinbefore defined) and, if desired, converting by methods known per se the PGE alicyclic ring (Z represents C=O) into that of a PGA (formula IV) compound. By the term "methods known per se" as used in this specification is meant methods heretofore used or described in the chemical literature.

The —OR⁴ groups of the compounds of formula VIII may be converted to hydroxy groups by mild hydrolysis with an aqueous solution of an organic acid, e.g. acetic acid or p-toluenesulphonic acid, or with a dilute inorganic acid, e.g. hydrochloric acid, for example by treatment of the compounds of formula VIII at a temperature ranging from ambient to 60° C. (preferably at a temperature below 45° C.) with an aqueous solution of an organic acid, e.g. acetic acid, or with a dilute inorganic acid, e.g. hydrochloric acid. The presence of an organic solvent miscible with water, for example a lower alkanol (e.g. methanol or ethanol) or tetrahydrofuran, assists the hydrolysis to proceed smoothly. In the case of cyclopentane derivatives of formula VIII wherein Z represented

it may be advantageous to esterify the compounds before hydrolysing the —OR⁴ groups using anhydrous p-toluenesulphonic acid in an absolute lower alkanol, and then to remove the ester moiety by methods known per se, for example by treatment of the resulting ester of a prostaglandin analogue of formula IX with an aqueous solution of an alkali metal (preferably sodium) hydroxide, and the salt obtained with an acid, e.g. hydrochloric acid.

The PGE compounds of formula IX (Z represents C=O) can be converted into corresponding PGA compounds of general formula VII, wherein A represents a grouping of formula IV, i.e. compounds of the formula:

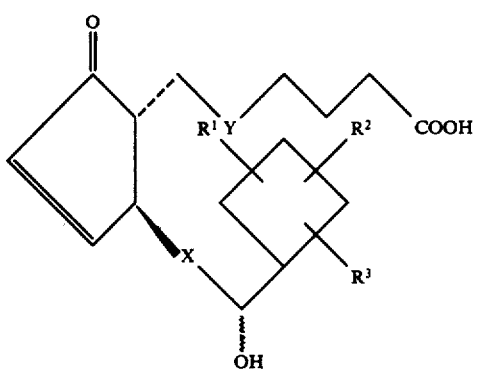

X (wherein the various symbols are as hereinbefore defined) by methods known per se, for example by subjecting the PGE's to dehydration using an aqueous solution of an organic or inorganic acid having a higher concentration than that employed for hydrolysis of compounds of general formula VIII, e.g. IN hydrochloric acid, if desired in the presence of cupric chloride, or acetic acid, and heating at a temperature of 30°–60° C.

It will be appreciated that PGA compounds conforming to general formula VII can be obtained directly from cyclopentane derivatives of formula VIII, wherein Z represents C=O, when such stronger acidic conditions are utilized to hydrolyze the —OR⁴ groups of starting materials of formula VIII as the intermediate PGE's of formula IX (Z represents C=O) will then be dehydrated in situ to PGA compounds.

The cyclopentane derivatives of general formula VIII employed as starting materials in the aforesaid process are new compounds and as such constitute a feature of the present invention. They can be prepared by the series of reactions depicted below:

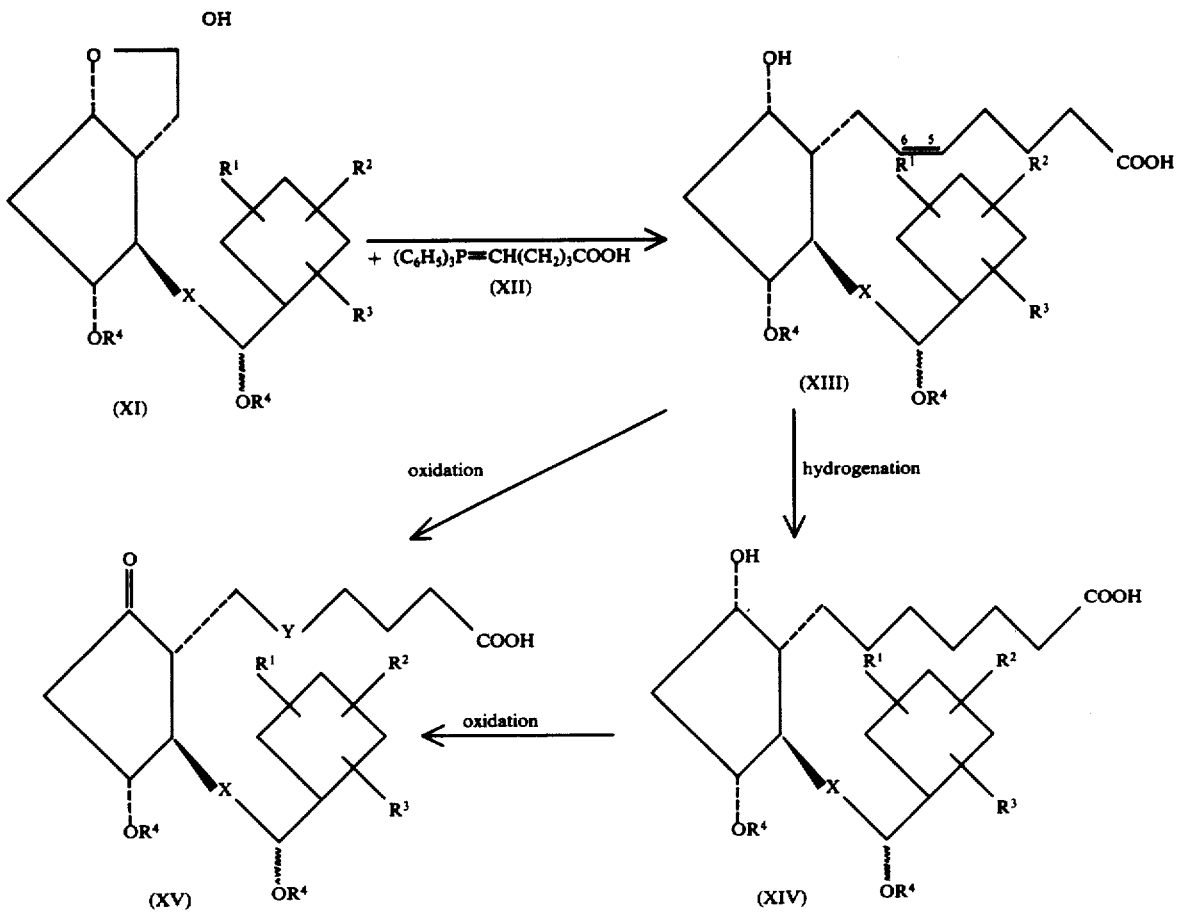

wherein X, Y, R¹, R², R³ and R⁴ are as hereinbefore defined.

The reaction between the bicyclo-octanes of formula XI and 4-carboxy-n-butylidenetriphenylphosphorane of formula XII [obtained by the reaction of sodiomethylsulphinylcarbanide with 4-carboxy-n-butyltriphenylphosphonium bromide, c.f. J. Amer. Chem. Soc., 91, 5675 (1969)] is carried out under the normal conditions utilized for effecting the Wittig reaction, e.g. in an inert solvent at ambient temperature. The reaction is preferably carried out in dimethylsulphoxide because the phosphorane compound is practically insoluble in other solvents, e.g. tetrahydrofuran, and because a cisdouble bond must be formed stereospecifically in the Wittig reaction. For the better performance of the Wittig reaction two to four molecular equivalents of the phosphorane compound are required for each mole of the bicyclo-octane reactant. The reaction is generally effected at a temperature of 10°–40° C., preferably at 20°–30° C., and is usually complete after about 1.5 to four hours at laboratory temperature. The acid product of formula XIII may be extracted from the reaction mixture by conventional procedures and further purified by column chromatography on silica gel.

Compounds of formula XIII may, if desired, be converted into corresponding compounds of formula XIV by reduction. Suitably, the reduction may be effected by catalytic hydrogenation in the presence of a hydrogenation catalyst and in the presence of an inert organic solvent, for example a lower alkanol, e.g. methanol and ethanol, at laboratory temperature at normal or elevated pressure, e.g. at a hydrogen pressure from atmospheric to 15 kilogrammes per square centimetre. When it is desired to reduce only the $C_5$–$C_6$ cis-vinylene group and leave unaffected a trans-vinylene group X, the hydrogenation catalyst may be, for example, palladium on charcoal, palladium black or a nickel catalyst, the hydrogenation being monitored to avoid any reduction of the trans-vinylene group X. When it is desired to reduce the $C_5$–$C_6$ cis-vinylene group of compounds of general formula XIII wherein X represents ethylene, the hydrogenation catalyst may be palladium on charcoal, palladium black, a nickel catalyst or platinum dioxide. When it is desired to reduce the $C_5$–$C_6$ cis vinylene group and X as trans-vinylene to obtain compounds of formula XIV wherein X represents ethylene, more active catalysts such as platinum black are required, and the hydrogenation is carried out until two times the molar quantity of hydrogen has been consumed.

The PGF compounds of formulae XIII and XIV may be converted to corresponding PGE compounds of formula XV by methods known per se for the conversion of a hydroxy group in the 9-position of a prostaglandin compound to an oxo group, for example by means of a chromic acid solution (e.g. obtained from chromium trioxide, manganese sulphate, sulphuric acid and water) or Jones' reagent.

The bicyclo-octane derivatives of formula XI can be prepared by the reaction sequence depicted below:

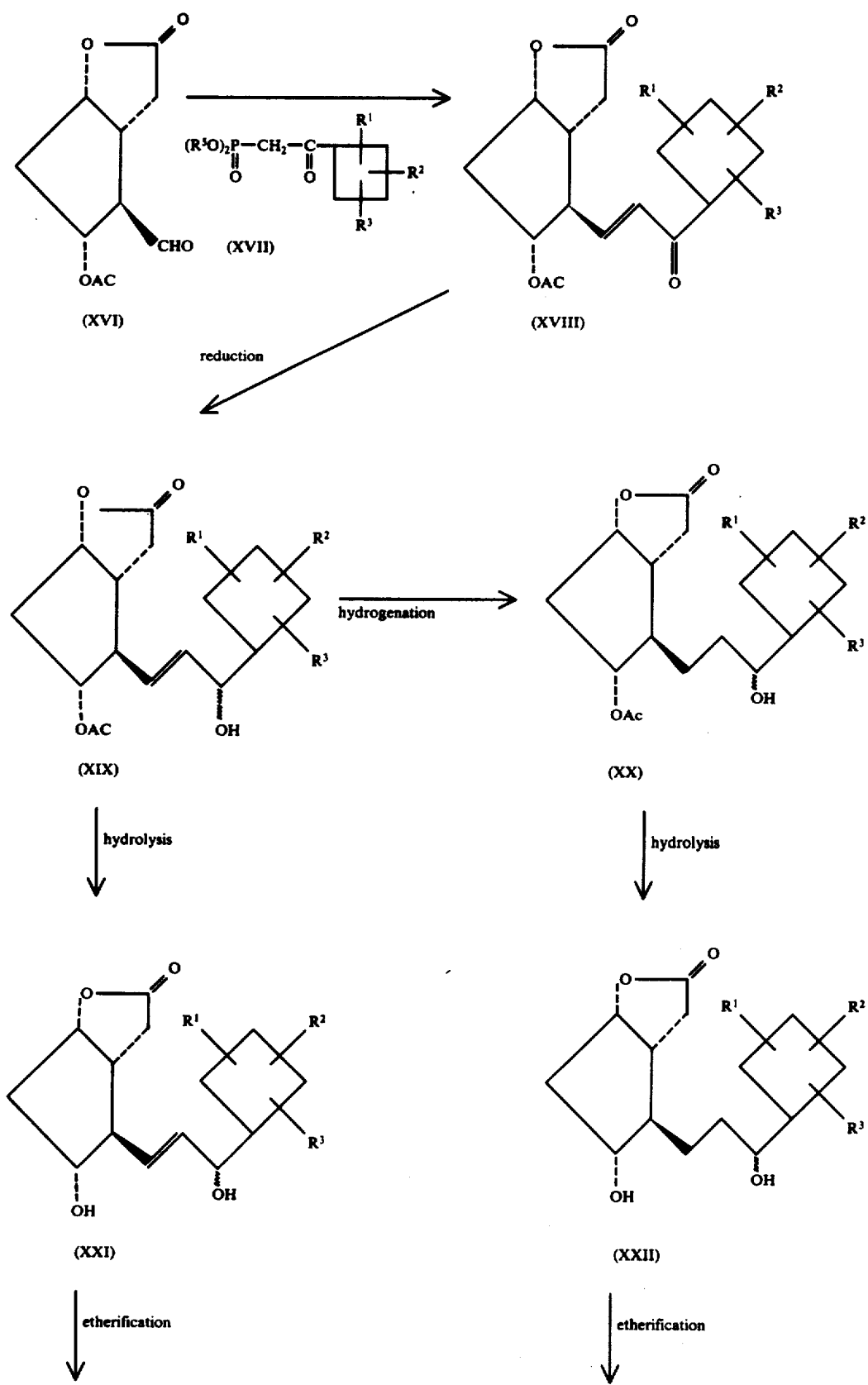

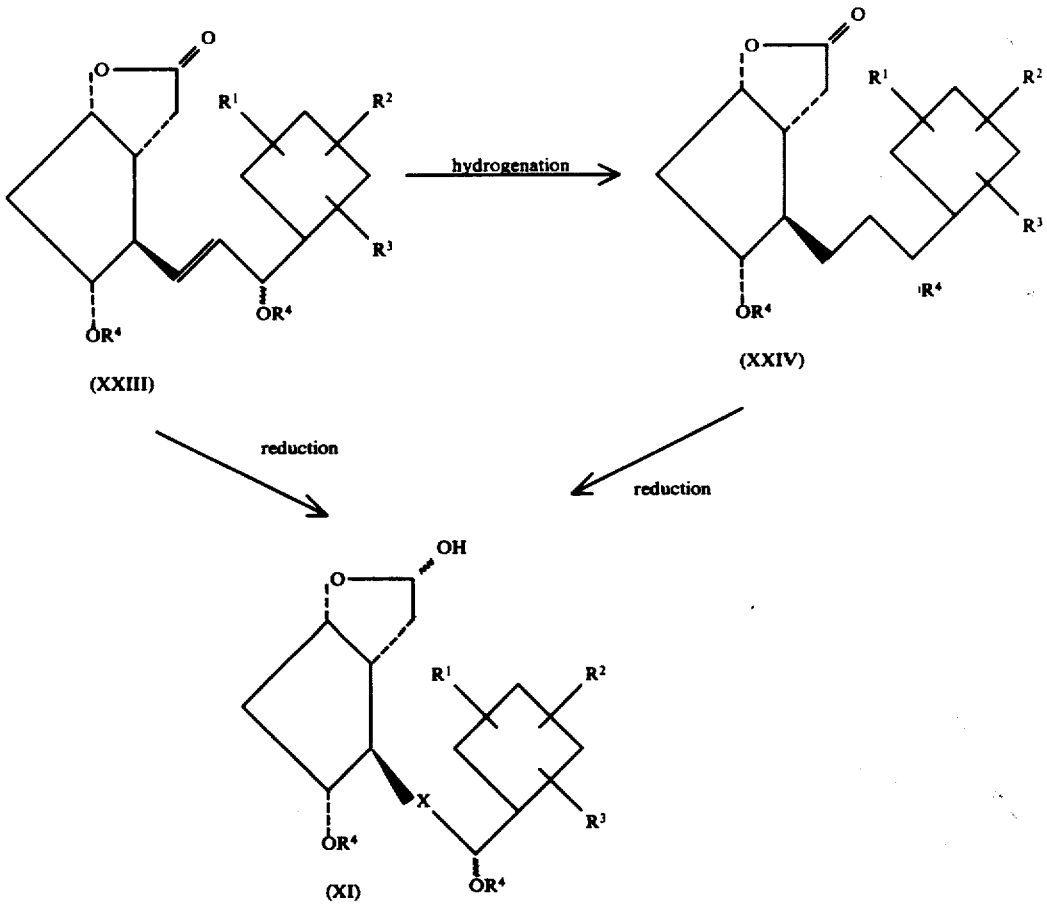

wherein X, R¹, R², R³ and R⁴ are as hereinbefore defined, Ac represents the acetyl group, and R⁵ represents a lower alkyl group.

The bicyclo-octane compound of formula XVI, viz. 1S-2-oxa-3-oxo-6R-formyl-7R-actoxy-cis-bicyclo[3,3,0]-octane, is a known compound, the racemic form being described in J. Amer. Chem. Soc., 91, 5675 (1969) and the natural form being described in J. Amer. Chem. Soc., 92, 397 (1970).

The phosphonates of formula XVII are initially converted to correspoding ylides by reaction with sodium hydride in an aprotic solvent, for example tetrahydrofuran or 1,2-dimethoxyethane, and the bicyclo-octane compound in solution in 1,2-dimethoxyethane or tetrahydrofuran is added to the ylide solution, and the ensuing Wittig reaction carried out at or about ambient temperature yields stereospecifically compounds of formula XVIII with a trans double bond. Those compounds are reduced with zinc borohydride in 1,2-dimethoxyethane or sodium borohydride in methanol-tetrahydrofuran to give compounds of formula XIX, the α- and β-hydroxy isomers of which can, if desired, be separated by column chromatography. Optionally, the bicyclo-octane compounds of formula XIX may be catalytically hydrogenated to corresponding compounds of formula XX by means heretofore mentioned for the hydrogenation of compounds of formula XIII to those of formula XIV. Hydrolysis of compounds of formula XIX or XX with, for example, an equimolar amount of anhydrous potassium carbonate in methanol at ambient temperature gives the diols of formula XXI or XXII respectively, which are then etherified to introduce groups R⁴ (R⁴ being as hereinbefore defined), for example by reaction with a dihydropyran (or vinyl ethyl ether or dihydrofuran) in methylene chloride at ambient temperature using p-toluenesulphonic acid as a catalyst, to give ethers of formula XXIII or XXIV. Optionally the bicyclo-octane compounds of formula XXIII may be catalytically hydrogenated to corresponding compounds of formula XXIV by means heretofore mentioned for the hydrogenation of compounds of formula XIII to those of formula XIV. Reduction of the ethers of formula XXIII or XXIV is then effected with diisobutylaluminium hydride in toluene at a low temperature, e.g. −70° C., and for 15–30 minutes to give the starting materials of formula XI.

The phosphonates of formula XVII can be prepared by the reaction sequence depicted below:

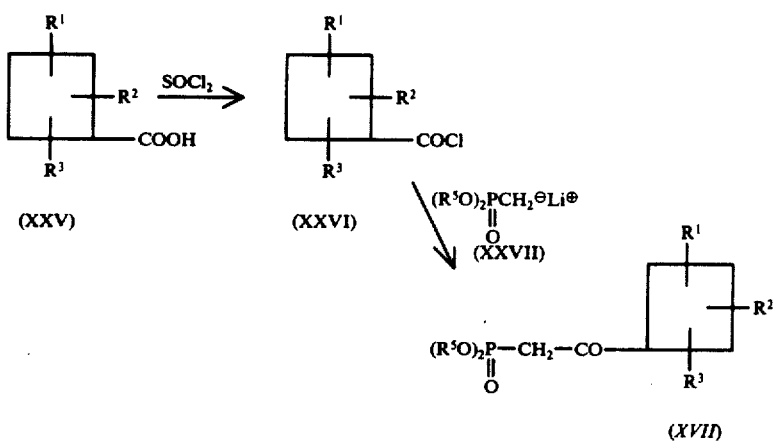

(XXV)　(XXVI)　(XVII)

wherein $R^1$, $R^2$, $R^3$ and $R^5$ are as hereinbefore defined.

The cyclobutane carboxylic acids of formula XXV are treated with thionyl chloride in manner known per se to give the corresponding acid chlorides of formula XXVI. The chlorides are treated with more than two molecular equivalents of the lithio derivative of dialkyl methylphosphonates of the formula $(R^5O)_2P(O)CH_3$, wherein $R^5$ is as hereinbefore defined, in an aprotic solvent, e.g. tetrahydrofuran, at a temperature at or below 0° C. to give the desired phosphonates of formula XVII.

The lithio derivatives of the dialkyl methylphosphonates of formula XXVII can be obtained by treatment of a dialkyl methylphosphonate in solution in tetrahydrofuran with n-butyllithium at a low temperature, e.g. −15° C. to −70° C. formula XXV are known compounds; the others can easily be obtained by adaptation of known methods for the preparation of cycloalkane carboxylic acids. Thus, 3,3-dimethylcyclobutane carboxylic acid is described in J. Chem. Soc., 1953, 3002; 1-phenylcyclobutane carboxylic acid is described in J. Amer. Chem. Soc. 63, 3538 (1941), and 2-methylcyclobutane carboxylic acid, 3-isopropylcyclobutane carboxylic acid and 3-n-butylcyclobutane carboxylic acid can be prepared by hydrolysis followed by thermal decarboxylation from corresponding cyclobutane-1,1-dicarboxylic acid esters respectively (the cyclobutane-1,1-dicarboxylic acid esters can themselves be prepared by the method described in J. Org. Chem., 21, 1371 (1956), Chem. Abst., 47, 9269a (1953) and Chem. Abst., 47 1225i (1953), respectively). In particular, cyclobutane carboxylic acids of formula XXV having an alkyl substituent on the carbon atom to which the carboxy radical is also attached can be obtained from cyclobutane carboxylic acids (cf. Org. Syn. Coll. Vol. 3, 213 (1955) by the reactions depicted schematically below:

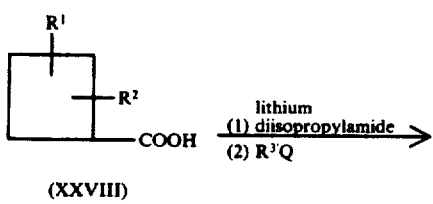

(XXVIII)

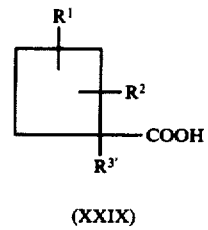

(XXIX)

wherein $R^1$ and $R^2$ are as hereinbefore defined, $R^{3'}$ represents a straight- or branched-chain alkyl group containing from 1 to 12 carbon atoms, and Q represents a halogen atom, e.g. bromine. Treatment of a cyclobutane carboxylic acid of formula XXVIII with more than two molecular equivalents of lithium diisopropylamide in an aprotic solvent, e.g. tetrahydrofuran, followed by treatment of the product, preferably in situ, with an alkyl halide of the formula $R^{3'}Q$ ($R^{3'}$ and Q being as hereinbefore defined) gives the 1-substituted-cyclobutane carboxylic acids of formula XXIX.

The prostaglandin analogues of general formula VII, wherein R represents a hydrogen atom and the other symbols are as hereinbefore defined, obtained by the hereinbefore described process can be converted into salts or alkyl esters having from 1 to 12 carbon atoms in the alkyl moiety.

The salts may be prepared from the compounds of general formula VII, wherein R represents a hydrogen atom, by methods known per se, for example by reaction of stoichiometric quantities of acids of general formula VII and the appropriate base, e.g. an alkali metal hydroxide or carbonate, ammonium hydroxide, ammonia or an amine, in a suitable solvent. The salts may be isolated by concentration of the solution, or if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the prostaglandins of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

Alkyl esters of the prostaglandins of general formula VII can be obtained by reaction of the acids with (i) diazoalkane compounds, e.g. diazomethane, (ii) alcohols or thiols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our British Pat. Nos. 1362956 and 1364125).

The prostaglandin analogues of general formula VII can also be converted into prostaglandin alcohols, i.e. compounds in which the carboxy radical is replaced by the hydroxymethylene (i.e. —CH$_2$OH) group, of the general formula:

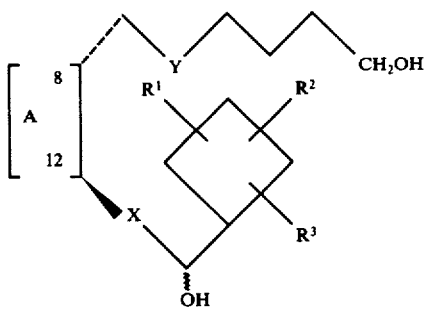

XXX wherein the various symbols are as hereinbefore defined.

The prostaglandin alcohols of general formula XXX can be prepared from the acids of general formula VII by application of the method described by Pike, Lincoln and Schneider in J. Org. Chem. 34, 3552–3557 (1967), for example by converting PGE and PGA acids of general formula VII into their methyl esters and then the esters into oximes by treatment with hydroxylamine, and reducing the oximes with lithium aluminium hydride to form oxime alcohols, and hydrolyzing them with, for example, acetic acid. PGF alcohols can be obtained directly by reducing methyl esters of PGF compounds of general formula VII with lithium aluminium hydride. The alcohol derivatives of prostaglandin analogues of general formula XXX possess pharmacological properties similar to the acids of general formula VII from which they are derived.

The prostaglandins of general formula VII, and corresponding alcohols of general formula XXX may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. α, β or γ-Cyclodextrins or mixtures thereof may be used in the preparation of the cyclodextrin clathrates. Conversion into their cyclodextrin clathrates serves to increase the stability of the prostaglandin compounds.

The prostaglandin analogues and cyclodextrin clathrates thereof according to the present invention possess the valuable pharmacological properties typical of prostaglandins in a selective fashion, including, in particular, activity on gastric acid secretion and bronchodilator activity, and are useful in the treatment of gastric ulceration and asthma. For example, in standard laboratory screening tests, (1) in rats in which gastric ulceration was induced by stress according to the method of Takagi and Okabe [Jap. J. Pharmac., 18, 9-18, (1968)], by oral administration, 16,16-propano-PGE$_1$ produces 68.9% and 89.4% inhibitions, respectively, of stress ulceration at doses of 50 and 100 μg./kg. animal body weight, respectively, 16,16-propano-PGE$_2$ produces 60.2% and 83.5% inhibitions, respectively, of stress ulceration at doses of 50 and 100 μg./kg. animal body weight, respectively, 16,16-propano-PGE$_1$ methyl ester produces 54.0% and 81.7% inhibitions, respectively, of stress ulceration at doses of 50 and 100 μg./kg. animal body weight, respectively, 16,16-propano-PGE$_2$ methyl ester produces 73.4% and 88.9% inhibitions, respectively, of stress ulceration at doses of 50 and 100 μg./kg. animal body weight, respectively, 16,16-propano-13,14-dihydro-PGE$_1$ produces 51.0% and 76.6% inhibitions, respectively, of stress ulceration at doses of 1000 and 2000 μg./kg. animal body weight, respectively, 16,16-propano-13,14-dihydro-PGE$_2$ produces 27.4% and 64.1% inhibitions, respectively, of stress ulceration at doses of 1000 and 2000 μg./kg. animal body weight, respectively, 16,16-propano-13,14-dihydro-PGE$_2$ methyl ester produces 10.9% inhibition of stress ulceration at a dose of 200 μg./kg. animal body weight, 16,16-propano-ω-nor-PGE$_2$ produces 13.7% and 37.1% inhibitions, respectively, of stress ulceration at doses of 100 and 200 μg./kg. animal body weight, respectively, 16,16-propano-ω-nor-PGE$_2$ methyl ester produces 1.2% and 13.4% inhibitions, respectively, of stress ulceration at doses of 100 and 200 μg./kg. animal body weight, respectively, 16,16-propano-ω-nor-13,14-dihydro-PGE$_1$ produces 27.1% and 39.3% inhibitions, respectively, of stress ulceration at doses of 1000 and 2000 μg./kg. animal body weight, respectively, 16,16-propano-ω-nor-13,14-dihydro-PGE$_2$ methyl ester produces 35.7% and 44.3% inhibitions, respectively, of stress ulceration at doses of 1000 and 2000 μg./kg. animal body weight, respectively, 16,16-propano-ω-homo-PGE$_2$ methyl ester produces 72.7% and 86.7% inhibitions, respectively, of stress ulceration at doses of 100 and 200 μg./kg. animal body weight, respectively, 16,16-propano-ω-dihomo-PGE$_2$ produces 45.3% and 62.2% inhibitions, respectively, of stress ulceration at doses of 100 and 200 μg./kg. animal body weight, respectively, 16,16-propano-ω-dihomo-PGE$_2$ methyl ester produces 41.8% and 66.1% inhibitions, respectively, of stress ulceration at doses of 100 and 200 μg./kg. animal body weight, respectively, and 16,16-propano-ω-nor-13,14-dihydro-PGE$_1$ methyl ester produces 16.2% inhibition of stress ulceration at a dose of 2000 μg./kg. animal body weight, and (2) when perfused into the stomach of the rat treated with pentagastrin at a dose of 2 μg./kg. animal body weight/hour, an increase in gastric pH from 2.0–2.5 to at least 4 in 50% of the pentagastrin-treated rats is produced by 16,16-propano-PGE$_1$ when administered at a dose of 0.07 μg./animal/minute, by 16,16-propano-PGE$_2$ when administered at a dose of 0.0175 μg./animal/minute, by 16,16-propano-PGE$_1$ methyl ester when administered at a dose of 0.30 μg./animal/minute, by 16,16-propano-PGE$_2$ methyl ester when administered at a dose of 0.06 μg./animal/minute, by 16,16-propano-13,14-dihydro-PGE$_1$ when administered at a dose greater than 10 μg./animal/minute, by 16,16-propano-13,14-dihydro-PGE$_2$ when administered at a dose of 5 to 10 μg./animal/minute, by 16,16-propano-ω-nor-PGE$_2$ when administered at a dose of 1.0 μg./animal/minute, by 16,16-propano-ω-nor-PGE$_2$ methyl ester when administered at a dose of 0.35 μg./animal/minute, by 16,16-propano-ω-nor-13,14-dihydro-PGE$_1$ when administered at a dose of 10 to 20 μg./animal/minute, and by 16,16-propano-ω-dihomo-PGE$_2$ when administered at a dose of less than 1.0 μg./animal/minute.

Preferred compounds of the invention are those compounds of general formula VII wherein R represents a hydrogen atom or a methyl group, and especially those such compounds wherein R$^1$, R$^2$ and R$^3$ each represent a hydrogen atom, an alkyl group containing from 1 to 6 carbon atoms or a phenyl group with the proviso that at least one of the symbols R$^1$, R$^2$ and R$^3$ represents an alkyl group containing from 1 to 6 carbon atoms or a phenyl group, and more particularly those such compounds wherein R$^1$ and R$^2$ represent hydrogen atoms and R$^3$ represents an alkyl group containing from 1 to 6 carbon atoms, preferably attached to the carbon atoms of the cyclobutane ring linked to the 15- position carbon atom carrying the hydroxy radical, and more especially those such compounds wherein A represents a grouping of formula II or IIIA, such as 16,16-propano-PGE$_1$, 16,16-propano-PGE$_2$, 16,16-propano-13,14-dihydro-PGE$_1$, 16,16-propano-13,14-dihydro-PGE$_2$, 16,16-propano-ω-nor-PGE$_2$, 16,16-propano-ω-nor-13,14-dihydro-PGE$_1$, 16,16-propano-ω-nor-13,14-dihydro-PGE$_2$, 16,16-propano-ω-homo-PGE$_2$ and 16,16-propano-ω-dihomo-PGE$_2$ and their methyl esters. Of outstanding interest is 16,16-propano-PGE$_2$.

The following Reference Examples and Examples illustrate the process of the present invention and products thereof. In the Examples 'IR', 'UV', 'NMR' and 'TLC' represent respectively 'Infrared absorption spectrum', 'Ultra-violet absorption spectrum', 'Nuclear magnetic resonance spectrum' and 'Thin layer chromatography'.

REFERENCE EXAMPLE 1 i. 2,2-Propanohexanoic acid

To a solution of tetrahydrofuran (hereinafter abbreviated to THF) (285 ml.) and diisopropylamine (56 g., 0.55 mol) in a dry, nitrogen-flushed flask, under an atmosphere of nitrogen, was added n-butyllithium (0.55 mol), in hexane and the mixture was magnetically stirred at such a rate as to maintain the temperature below 0° C. To the cold basic solution, cyclobutane carboxylic acid (26 g., 0.26 mol) was added. After stirring for 30 minutes below 0° C., the reaction mixture was treated with n-butyl bromide (38 g., 0.28 mol) and, after stirring for a further 2 hours at room temperature, was worked up in the following manner. The reaction mixture was acidified to about pH 1 with dilute hydrochloric acid (10%) at 0° C. and extracted with petroleum ether. The extract was washed with dilute hydrochloric acid (100 ml. × 5), water, and a saturated aqueous solution of sodium chloride. After drying over sodium sulphate, the extract was concentrated and distilled in vacuo to give liquid 2,2-propanohexanoic acid: first fraction (1.7 g.) b.p. 85°-100° C/5 mm.Hg, main fraction (2.4 g.; b.p. 110°-115° C/5 mm.Hg) were both shown to be an alkylated product by NMR and IR spectroscopy:

NMR (C Cl$_4$): δ; 12.01 (1H, D$_2$O exchanged), 2.75-2.25

(2H, multiplet), 2.13-1.66 (6H, multiplet), 1.52-1.05

(4H, multiplet), 0.93 (3H, triplet, J=6,5Hz);

IR (liquid film): ν; 3700-2300, 1700 cm$^{-1}$;

Mass spectrum (as methyl ester): m/e = 170(M$^+$), 142 (M$^+$−28), 139 (M$^+$−31), 127 (M$^+$−43), 114 (M$^+$−56).

ii. 2,2-Propanopentanoic acid

Proceeding as described in Reference Example 1(i) using 30.0 g. of cyclobutane carboxylic acid and 44.2 g. of n-propyl bromide, there were obtained 35.0 g. (yield 82.2%) of the title compound having the following physical characteristics:

b.p. 102° − 108° C./3.0 − 3.5 mm.Hg;

NMR (CDCl$_3$): δ; 11.08 (1H, broad singlet), 2.41 −2.25

(2H, multiplet), 0.89 (3H, broad triplet);

IR (liquid film): ν; 3500 - 2300, 1705 cm$^{-1}$;

Mass spectrum: m/e = 143 (M$^+$+1), 142 (M$^+$), 125 (M$^+$−17), 113 (M$^+$−29).

iii. 2,2-Propanoheptanoic acid

Proceeding as described in Reference Example 1(i) using 20.0 g. of cyclobutane carboxylic acid and 29.7 g. of n-pentyl bromide, there were obtained 24.0 g. (yield 70.9%) of the title compound having the following physical characteristics:

NMR (CDCl$_3$): δ; 10.50 (1H, broad singlet), 2.62 − 2.31

(2H, multiplet), 2.12 − 1.65 (6H, multiplet), 1.48 − 1.14

(6H, multiplet), 0.89 (3H, triplet, J=6.0 Hz);

IR (liquid film): ν; 3500 − 2300, 1700 cm$^{-1}$;

Massspectrum: m/e = 171 (M$^+$+1), 170 (M$^+$), 153 (M$^+$−17), 141 (M$^+$−29).

iv. 2,2-Propanooctanoic acid

Proceeding as described in Reference Example 1(i) using 9.00 g. of cyclobutane carboxylic acid and 16.0 g. of n-hexyl bromide, there were obtained 22.0 g. of crude product which was purified by column chromatography on silica gel using benzene as eluant to obtain the title compound (15.6 g.; quantitative yield) as a yellow liquid having the following physical characteristics:

NMR (CDCl$_3$): δ; 9.47 (1H, broad singlet, D$_2$O exchanged), 2.60 − 2.25 (2H, multiplet), 2.10 − 1.60 (6H, multiplet), 1.47 − 1.10 (8H, multiplet), 0.89 (3H, broad triplet);

IR (liquid film): ν; 3400 − 2300, 1700 cm$^{-1}$;

Mass spectrum: m/e = 184 (M$^+$), 155, 141, 113, 100, 87, 70, 55,41.

REFERENCE EXAMPLE 2 i. 2,2-Propanohexanoyl chloride

Freshly distilled thionyl chloride was added to 2,2-propanohexanoic acid (28 g., prepared as described in Reference Example 1(i)). After stirring for 1.5 hours at room temperature, the temperature of the reaction mixture was raised to 75° C. and kept at that temperature for 2 hours. After removal of thionyl chloride under reduced pressure, the oily residue was distilled in vacuo to give in almost quantitative yield 2,2-propanohexanoyl chloride having the following physical characteristics:

b.p. ~ 50° C./1 mm.Hg;
IR (liquid film): ν; 1800 cm⁻¹.

In a similar manner there may be prepared cyclobutanecarbonyl chloride, 2,3-dimethylcyclobutanecarbonyl chloride, 1-phenylcyclobutanecarbonyl chloride, 2-methylcyclobutanecarbonyl chloride, 3-isopropylcyclobutanecarbonyl chloride and 3-n-butylcyclobutanecarbonyl chloride, from the corresponding acids.

ii. 2,2-Propanopentanoyl chloride

Proceeding as described in Reference Example 2(i) using 35.0 g. of 2,2-propanopentanoic acid, prepared as described in Reference Example 1(ii), there were obtained 36.3 g. (yield 92%) of the title compound having the following physical characteristics:

b.p. 30° - 35° C./3 mm.Hg.
IR (liquid film): ν; 1800 cm⁻¹.

iii. 2,2-Propanoheptanoyl chloride

Proceeding as described in Reference Example 2(i) using 24.0 g. of 2,2-propanoheptanoic acid, prepared as described in Reference Example 1(iii), there were obtained 25.5 g. (quantitative yield) of the title compound having the following physical characteristics:

b.p. ~ 65° C./1 mm.Hg;
IR (liquid film): ν; 1800 cm⁻¹.

iv. 2,2-Propanooctanoyl chloride

Proceeding as described in Reference Example 2(i) using 16.1 g. of 2,2-propanooctanoic acid, prepared as described in Reference Example 1(iv) there were obtained 15.7 g. (yield 95%) of the title compound having the following physical characteristics:

b.p. 100° - 101° C./2 mm.Hg;
IR (liquid film): ν; 1800 cm⁻¹.

REFERENCE EXAMPLE 3 i. Dimethyl 2-oxo-3,3-propanoheptylphosphonate

A solution of dimethyl methylphosphonate (54 g.) in THF (300 ml.) was treated with n-butyllithium in hexane (2.3 equivalents relative to the phosphate) for 30 minutes at −70° C. under an atmosphere of nitrogen. The reaction mixture was further treated with 2,2-propanohexanoyl chloride (32 g., prepared as described in Reference Example 2(i)) in THF (300 ml.) for 5 minutes at −70° C. After stirring for 30 minutes at −70° C. and for 1 hour at room temperature, the reaction mixture was worked up in the following manner: The reaction mixture was acidified with glacial acetic acid (25 ml.), and then concentrated under reduced pressure. The residue was dissolved in water (50 ml.) and extracted with diethyl ether (100 ml. × 5). The aqueous layer was concentrated under reduced pressure, and extracted again with diethyl ether (50 ml. × 3). The combined organic layers were dried over magnesium sulphate, concentrated and distilled in vacuo to yield 34 g. (yield 70%) of dimethyl 2-oxo-3,3-propanoheptylphosphonate having the following physical characteristics:

b.p. 119° - 123° C./1 mm.Hg;
NMR (C Cl₄): δ; 3.75 (6H, doublet, J=11.0 Hz), 2.91 (2H, doublet, J=22.0 Hz), 2.55 − 2.30 (2H, multiplet),
2.00 − 1.00 (10H, multiplet), 0.91 (3H, triplet, J=7.0 Hz),
IR (liquid film): ν; 1705, 1260, 1040 cm⁻¹;
Mass spectrum: m/e = 262 (M⁺), 206 (M⁺−56), 151 (M⁺−111), 124 (M⁺−138).

In a similar manner there may be prepared dimethyl 2-oxo-2-cyclobutylethylphosphonate, dimethyl 2-oxo-3,5-methano-5-methylhexylphosphonate, dimethyl 2-oxo-3-phenyl-3,4-ethanobutylphosphonate, dimethyl 2-oxo-3,4-ethanopentylphosphonate and dimethyl 2-oxo-3,5-methanononylphosphonate from the corresponding carbonyl chlorides.

ii. Dimethyl 2-oxo-3,3-propanohexylphosphonate

Proceeding as described in Reference Example 3(i) using 32.4 g. of 2,2-propanopentanoyl chloride, prepared as described in Reference Example 2(ii) there were obtained 39.2 g. (yield 78%) of the title compound having the following physical characteristics:

b.p. 117°-122° C./2 mm.Hg;
NMR (CDCl₃): δ; 3.70 (6H, doublet, J=11.0 Hz), 2.97 (2H, doublet, J=22.0 Hz), 2.52 − 2.20 (2H, m), 1.90 − 1.60 (6H, multiplet), 1.26 − 1.00 (2H, multiplet), 0.90 (3H, triplet, J=6.5 Hz);
IR (liquid film): ν; 3450, 1705, 1260, 1060, 1040 cm⁻¹;
Mass spectrum: m/e = (M⁺), 206 (M⁺−42), 151 (M⁺−97), 124 (M⁺−124), 94 (M⁺−154).

iii. Dimethyl 2-oxo-3,3-propanooctylphosphonate

Proceeding as described in Reference Example 3(i) using 25.7 g. of 2,2-propanoheptanoyl chloride, prepared as described in Reference Example 2(iii), there were obtained 35.1 g. (yield 93%) of the title compound having the following physical characteristics:

b.p. ~153° C./~1 mm.Hg;
NMR (CDCl₃): δ; 3.81 (6H, doublet, J=11.0 Hz), 3.04 (2H, doublet, J=22.0 Hz), 2.55 − 2.28 (2H, multiplet), 1.95 − 1.65 (6H, multiplet), 1.39 − 1.06 (6H, multiplet), 0.88 (3H, broad triplet);
IR (liquid film): ν; 1705, 1260, 1035 cm⁻¹;
Mass spectrum: m/e = 276 (M⁺), 219 (M⁺−57), 124 (M⁺−152).

iv. Dimethyl 2oxo-3,3-propanononylphosphonate

Proceeding as described in Reference Example 3(i) using 15.7 g. of 2,2-propanooctanoyl chloride, prepared as described in Reference Example 2(iv), and purifying the crude product by column chromatography on silica gel (200 g.) using a mixture of ethyl acetate and benzene (1:2) as eluant, there were obtained 21.7 g. (yield 90%) of the title compound (a yellow liquid) having the following physical characteristics:

NMR (CCl₄): δ; 3.74 (6H, doublet, J=11.0 Hz), 2.92 (2H, doublet, J=22.0 Hz), 2.54 − 2.23 (2H, multiplet), 2.00 − 1.55 (6H, multiplet), 1.37 − 1.10 (8H, multiplet), 0.88 (3H, broad triplet);
IR (liquid film): ν; 1705, 1260, 1040 cm⁻¹;
Mass spectrum: m/e = 291 (M⁺+1), 290 (M⁺), 127, 126, 125, 124, 110, 109.

REFERENCE EXAMPLE 4 i.
1S-2-Oxa-3-oxo-6R-(3-oxo-4,4-propanooct-trans-1-enyl)-7R-acetoxy-cis-bicyclo[3,3,0]octane Anhydrous pyridine (19.1 ml.) and chromium trioxide (11.6 g., 116 mmol) were added to methylene chloride (310 ml.) at 10°-20° C. and stirred for 15 minutes. The reaction mixture was treated with Celite 545 (22 g.) and cooled to 0° C. 1S-2-Oxa-3-oxo-6R-hydroxymethyl-7R-acetoxy-cis-bicyclo[3,3,0]octane (4.7 g., 21.8 mmol) [prepared as described in J. Amer. Chem. Soc. 92, 397 (1970] in methylene chloride (20 ml.) was oxidized using the chromium trioxide solution prepared as described above with stirring for 15 minutes at 0° C. After addition of sodium bisulphate monohydrate (85.5 g.), the mixture was stirred for an additional 10 minutes and then filtered through a pad of magnesium sulphate at 0° C. After washing the solids with cold methylene chloride, the solution was concentrated using a rotary evaporator (0° C.) to afford the crude aldehyde, which was used immediately in the next step.

To a suspension of sodium hydride (592 mg., 24.6 mmol) in 1,2-dimethoxyethane was added a solution of dimethyl 2-oxo-3,3-propanoheptylphosphonate (6.4 g., 24.4 mmol, prepared as described in Reference Example 3(i)) in 1,2-dimethoxyethane (117 ml.). The mixture was stirred at room temperature for 30 minutes, by which time no further hydrogen was evolved. To the reaction mixture was added the crude aldehyde (obtained as described above) in 1,2-dimethoxyethane (117 ml.) at 3°-5° C., and the mixture was stirred at room temperature for 40 minutes. After neutralizing excess base with glacial acetic acid, the solvent was removed under reduced pressure (<30° C.). The residue was dissolved in water and extracted with ethyl acetate. The organic layer was washed with water, dried over magnesium sulphate, and concentrated to give an oily product. The oily product was chromatographed on silica gel (100 g.) to yield the title compound (3.3 g., 44% yield based on 1S-2-oxa-3-oxo-6R-hydroxymethyl-7R-acetoxy-cis-bicyclo[3,3,0]-octane by elution with benzene:ethyl acetate, 8:1) having the following physical characteristics:

NMR (CDCl$_3$): δ; 6.64 (1H, double doublet, J=15.0 Hz,
J=8.0 Hz), 6.28 (1H, doublet, J=15.0 Hz), 4.87 — 5.12 (2H, multiplet), 1.99 (3H, singlet), 0.88 (3H, triplet,
J=6.5 Hz);
IR (CHCl$_3$): ν; 1780, 1745, 1695, 1635, 1245, 990 cm$^{-1}$;
Mass Spectrum: m/e = 348 (M+), 292 (M+ −56), 288 (M+ −60);
UV: $\lambda_{max}^{MeOH}$ = 226 Mμ(ε 11,500);
Optical rotation: $[\alpha]_D^{25}$ = −13.1° (C=2.44, CHCl$_3$).

In a similar manner there may be prepared 1S-2-oxa-3-oxo-6R-(3-oxo-4,6-methano-6-methylhept-trans-1-enyl)-7R-acetoxy-cis-bicyclo[3,3,0]octane, 1S-2-oxa-3-oxo-6R-(3-oxo-4-phenyl-4,5-ethanopent-trans-1-enyl)-7R-acetoxy-cis-bicyclo[3,3,0]octane, 1S-2-oxa-3-6R-(3-oxo-4,5-ethanohex-trans-1-enyl)-7R-acetoxy-cis-bicyclo[3,3,0]octane and 1S-2-oxa-3-oxo-6R-(3-oxo-4,6-methanodec-trans-1-enyl)-7R-acetoxy-cis-bicyclo[3,3,0]octane using the appropriate phosphonates.

ii.
1S-2-Oxa-3-oxo-6R-(3-oxo-4,4-propanohept-trans-1-enyl)-7R-acetoxy-cis-bicyclo[3,3,0]octane Proceeding as described in Reference Example 4(i) using 10.3 g. of dimethyl 2-oxo-3,3-propanohexylphosphonate, prepared as described in Reference Example 3(ii), there were obtained 3.62 g. (yield 29.4% based on 1S-2-oxa-3-oxo-6R-hydroxymethyl-7R-acetoxy-cis-bicyclo[3,3,0]octane) of the title compound having the following physical characteristics:

NMR (CDCl$_3$): δ; 6.71 (1H, double doublet, J=15.5 Hz,
J=8.0 Hz), 6.31 (1H, doublet, J=15.5 Hz), 5.14−4.88 (2H, multiplet), 2.04 (3H, singlet), 0.88 (3H, broad triplet);
IR (CHCl$_3$): ν; 1775, 1740, 1690, 1630, 985 cm$^{-1}$;
UV: $\lambda_{max}^{MeOH}$ = 227 mμ (ε 13,100);
Mass spectrum: m/e 275 (M+ −59), 274 (M+ −60);
m.p. 71°-72° C.

iii.
1S-2-Oxa-3-oxo-6R-(3-oxo-4,4-propanonon-trans-1-enyl)-7R-acetoxy-cis-bicyclo[3,3,0]octane Proceeding as described in Reference Example 4(i) using 11.0 g. of dimethyl 2-oxo-3,3-propanooctylphosphonate, prepared as described in Reference Example 3(iii), there was obtained 4.28 g. (yield 31.7% based on 1S-2-oxa-3-oxo-6R-hydroxymethyl-7-acetoxy-cis-bicyclo[3,3,0]octane) of the title compound having the following physical characteristics:

NMR (CDCl$_3$): δ; 6.72 (1H, double doublet, J=15.0 Hz, p1 J=7.5 Hz), 6.32 (1H, doublet, J=15.0 Hz), 5.16−4.93 (2H, multiplet), 2.03 (3H, singlet), 0.86 (3H, broad triplet);
IR (CHCl$_3$): ν; 1770, 1745, 1690, 1630, 1240, 990, 935 cm$^{-1}$;
Mass spectrum: m/e = 362 (M+), 302 (M+ −60), 292 (M+ −70), 232 (M+ −130);
UV: $\lambda_{max}^{MeOH}$ = 227 mμ (ε 14,200);
Optical rotation: $[\alpha]_D^{22}$ = −7.16° (C = 1.69, CHCl$_3$);
m.p. 74°-75° C.

iv.
1S-2-Oxa-3-oxo-6R-(3-oxo-4,4-propanodec-trans-1-enyl)-7R-acetoxy-cis-bicyclo[3,3,0]octane Proceeding as described in Reference Example 4(i) using 12.1 g. of dimethyl 2-oxo-3,3-propanononylphosphonate, prepared as described in Reference Example 3(iv), there were obtained 5.0 g. (yield 35% based on 1S-2-oxa-3-oxo-6R-hydroxymethyl-7R-acetoxy-cis-bicyclo[3,3,0]octane) of the title compound as a yellow oil, which was purified by recrystallization from diisopropyl ether to yield 3.4 g. of white crystals having the following physical characteristics:

NMR (CDCl$_3$): δ; 6.72 (1H, double doublet, J=15.0 Hz,
J=7.5 Hz), 6.31 (1H, doublet, J=15.0 Hz), 5.14−4.90 (2H, multiplet), 2.63−2.15 (6H, multiplet), 2.03 (3H, singlet), 1.97−1.65 (6H, multiplet), 1.35−1.10 (8H, multiplet), 0.95−0.75 (3H, broad triplet);
IR (CHCl$_3$): ν; 1780, 1745, 1690, 1630, 1240, 980 cm$^{-1}$;
Mass spectrum: m/e = 376 (M+), 317, 316, 292, 288, 232;
UV: $\lambda_{max}^{MeOH}$ = 229 Mμ (ε 6320);
Optical rotation: $[\alpha]_D^{22}$ = −11.1° (C = 1.74, CHCl$_3$);
m.p. 92°-93° C.

REFERENCE EXAMPLE 5 i. 1S-2-Oxa-3-oxo-6R-(3R (and 3S)-hydroxy-4,4-propanooct-trans-1-enyl)-7R-acetoxy-cis-bicyclo[3,3,0]octane To a solution of 1S-2-oxa-3-oxo-6R-(3-oxo-4,4-propanooct-trans-1-enyl)-7R-acetoxy-cis-bicyclo[3,3,0]-octane (2.9 g., 8.35 mmol prepared as described in Reference Example 4(i)) in absolute methanol (57 ml.) and anhydrous THF (29 ml.) was gradually added sodium borohydride (1.54 g., 40.6 mmol) at −30° C. After stirring for 15 minutes, the reaction mixture was quenched by addition of glacial acetic Acid (5.1 ml.), and concentrated. The residue was dissolved in water and the solution extracted with chloroform. The extract was dried over sodium sulphate and concentrated to yield an oily product (3.0 g.). After removal of excess acetic acid in vacuo, the crude residue was purified by column chromatography on silica gel (300 g.) using a mixture of diethyl ether and hexane (8:2) as eluant. The following fractions were collected.

a. 1.18 g. (desired 3R-alcohol)
b. 1.00 g. (mixture of 3R- and 3S-alcohols)
c. 0.700 g. (3S-alcohol) The fraction (b) was further purified by additional column chromatography on silica gel (100 g.) to yield
d. 0.230 g. (3R-alcohol)
e. 0.710 g. (Mixture of 3R- and 3S-alcohols)
f. 0.032 g. (3S-alcohol)

1. 3R-alcohol has the following physical characteristics:
NMR (CDCl$_3$): δ; 5.70−5.50 (2H, multiplet), 5.10−4.87 (2H, multiplet), 4.04 (1H, doublet, J=5.0 Hz), 2.04 (3H, singlet), 0.92 (3H, triplet);
IR (CHCl$_3$): ν; 3500, 1775, 1740 1250, 980 cm$^{-1}$;
Mass spectrum: m/e = 351 (M$^+$+1), 350 (M$^+$), 273 (M$^+$+1−78), 272 (M$^+$−78);
Optical rotation: [α]$_D^{24}$ = = 14.8° (C=1.63, CHCl$_3$).

2. 3S-alcohol has the following physical characteristics:
NMR (CDCl$_3$): δ; 5.83−5.42 (2H, multiplet), 5.07−4.79 (1H, multiplet), 4.24−3.80 (2H, multiplet), 0.91 (3H, triplet);
IR (CHCl$_3$): ν; 3450, 1770, 980 cm$^{-1}$;
Mass spectrum: m/e = 290 (M$^+$−18), 198 (M$^+$+1−111);
Optical rotation: [α]$_D^{23}$ = −41.0° (C = 1.45, CHCl$_3$).

ii. 1S-2-Oxa-3-oxo-6R-(3R-hydroxy-4,4-propanooctyl)-7R-acetoxy-cis-bicyclo[3,3,0]octane 1.13 g. of 1S-2-oxa-3-oxo-6R-(3R-hydroxy-4,4-propanooct-trans-1-enyl)-7R-acetoxy-cis-bicyclo[3,3,0]-octane, prepared as described in Reference Example 5(i), in 34.5 ml. of methanol were subjected to catalytic hydrogenation in the presence of 374 mg. of 5% w/w palladium on carbon. Catalytic reduction of the starting material was carried out at room temperature and atmospheric pressure for 1 hour and 20 minutes. After the hydrogenation, the catalyst was filtered off and the resulting filtrate was evaporated to dryness under reduced pressure to give 720 mg. (yield 63%) of the title compound. The NMR spectrum shows the absence of the signals due to two hydrogens of a double bond near to δ = 5.50 ppm. The title compound has the following physical characteristics: NMR (CDCl$_3$): δ; 5.15−4.93 (2H, multiplet), 3.58 −3.40 (1H, multiplet), 2.05 (3H, singlet), 0.96 (3H, broad triplet);
IR (CHCl$_3$):ν; 3455, 1770, 1730, 1300−1200, 1180, 1070, 1050 cm$^{-1}$;
Mass spectrum: m/e = 292 (M$^+$−60), 241 (M$^+$−111), 181 (M$^+$−171);
Optical rotation: [α]$_D^{26}$ = − 21.9° (C = 1.26, CHCl$_3$).

iii. 1S-2-Oxa-3-oxo-6R-(3R (and 3S)-hydroxy-4,4-propanohept-trans-1-enyl)-7R-acetoxy-cis-bicyclo[3,3,0]-octane Proceeding as described in Reference Example 5(i) using 6.40 g. of 1S-2-oxa-3-oxo-6R-(3-oxo-4,4-propanohept-trans-1-enyl)-7R-acetoxy-cis-bicyclo[3,3,0]-octane, prepared as described in Reference Example 4(ii) the title compounds were obtained in the following yields:

| 3R-alcohol | 2.59 g. |
|---|---|
| 3R- and 3S-alcohols mixture | 2.51 g. |
| 3S-alcohol | 2.48 g. |

1. 3R-alcohol has the following physical characteristics:
NMR (CDCl$_3$): δ; 5.68−5.52 (2H, multiplet), 5.09−4.85 (2H, multiplet), 4.03 (1H, doublet, J=5.0 Hz), 2.03 (3H, singlet), 1.00−0.80 (3H, multiplet);
IR (CHCl$_3$): ν ; 3500, 1770, 1740, 1240, 980 cm$^{-1}$;
Mass spectrum: m/e = 276 (M$^+$−60);
Optical rotation: [α]$_D^{22}$ = −14.8° (C = 0.91, CHCl$_3$).

2. 3S-alcohol has the following physical characteristics:
NMR (CDCl$_3$): δ; 5.82−5.40 (2H, multiplet), 5.09−4.87 (2H, multiplet), 4.03 (1H, doublet, J=5.0 Hz), 2.04 (3H, singlet), 1.00−0.82 (3H, multiplet);
IR (CHCl$_3$): ν; 3500, 1770, 1735, 1240, 980 cm$^{-1}$;
Mass spectrum: m/e = 337 (M$^+$+1), 336 (M$^+$), 276 (M$^+$−60);
Optical rotation [α]$_D^{17}$ = − 21.7° (C = 1.19, CHCl$_3$).

iv. 1S-2-Oxa-3-oxo-6R-(3R (and 3S)-hydroxy-4,4-propanonontrans-1-enyl)-7R-acetoxy-cis-bicyclo[3,3,0]octane Proceeding as described in Reference Example 5(i) using 4.13 g. of 1S-2-oxa-3-oxo6R-(3-oxo-4,4-propano-non-trans-1-enyl)-7R-acetoxy-cis-bicyclo[3,3,0]-octane, prepared as described in Reference Example 4(iii), the title compounds were obtained in the following yields:

| 3R-alcohol | 1.13 g. |
|---|---|
| 3R- and 3S-alcohols mixture | 2.02 g. |
| 3S-alcohol | 0.75 g. |

1. 3R-alcohol has the following physical characteristics:
NMR (CDCl$_3$): δ; 5.67−5.56 (2H, multiplet), 5.08−4.87 (2H, multiplet), 4.02 (1H, doublet, J=5.0 Hz), 2.04 (3H, singlet), 0.89 (3H, broad triplet);
IR (CHCl$_3$): ν; 3600−3300, 1770, 1730, 1240, 970 cm$^{-1}$;
Mass spectrum: m/e = 365 (M$^+$+1), 364 (M$^+$), 305 (M$^+$−59), 304 (M$^+$−60);
Optical Rotation: [α]$_D^{21}$ = − 14.1° (C = 1.60, CHCl$_3$).

2. 3S-alcohol has the following physical characteristics:

NMR (CDCl$_3$): δ; 5.68−5.54 (2H, multiplet) 5.07−4.86
(2H, multiplet), 4.02 (1H, doublet, J=5.0 Hz), 2.04 (3H, singlet), 0.89 (3H, triplet, J=6.0 Hz);
IR (CHCl$_3$): ν; 3600−2300, 1770, 1735, 1240, 980 cm$^{-1}$;
Mass spectrum: m/e 365 (M$^+$+1), 364 (M$^+$), 346 (M$^+$−18),
305 (M$^+$−59), 304 (M$^+$−60);
Optical rotation: [α]$_D^{21}$ = − 24.6° (C = 3.32, CHCl$_3$).

v. 1S-2-Oxa-3-oxo-6R-(3R (and 3R)-hydroxy-4,4-propanodec-trans-1-enyl)-7R-acetoxy-cis-bicyclo[3,3,0]octane Proceeding as described in Reference Example 5(i), using 3.4 g. of 1S-2-oxa-3-oxo-6R-(3-oxo-4,4-propano-dec-trans-1-enyl)-7R-acetoxy-cis-bicyclo[3,3,0]-octane, prepared as described in Reference Example 4(iv), the title compounds were obtained in the following yields:- (1.60 g. of enone compound were recovered).

| 3R-alcohol | 900 mg. |
| 3R- and 3S-alcohols mixture | 550 mg. |
| 3S-alcohol | 350 mg. |

1. 3R-alcohol has the following physical characteristics:-

NMR (CDCl$_3$): δ; 5.81-5.42 (2H, multiplet), 4.59-4.35 (2H, multiplet), 4.01 (1H, doublet, J=5.0 Hz), 2.92-2.32 (6H, multiplet), 2.02 (3H, singlet), 2.08 (1H, broad singlet, D$_2$O exchanged), 2.20-1.58 (6H, multiplet), 1.43-1.15 (10H, multiplet), 0.89 (3H, broad triplet); IR (CHCl$_3$): ν; 3500, 1775, 1740, 1240, 980 cm$^{-1}$;
Mass spectrum: m/e = 378 (M$^+$), 360 (M$^+$−18), 318 (M$^+$−60), 301, 300 (M$^+$−78), 180;
Optical rotation: [α]$_D^{20}$ = − 12.0° (C= 2.13, CHCl$_3$).

2. 3S-alcohol has the following physical characteristics:-

NMR (CDCl$_3$): δ; 5.67-5.55 (2H, multiplet), 5.10-4.85 (2H, multiplet), 4.01 (1H, doublet, J=5.0 Hz), 2.90-2.35 (6H, multiplet), 2.03 (3H, singlet), 1.94 (1H, broad singlet, D$_2$O exchanged), 2.18-1.55 (6H, multiplet), 1.45-1.15 (10H, multiplet), 0.90 (3H, broad triplet);
IR (CHCl$_3$): ν; 3450, 1775, 1740, 1240, 980 cm$^{-1}$;
Mass spectrum: m/e 32 378 (M$^+$), 360 (M$^+$−18), 318 (M$^+$−60), 301, 300 (M$^+$−78), 180;
Optical rotation: [α]$_D^{20}$ = − 25.8° (C = 1.40, CHCl$_3$).

REFERENCE EXAMPLE 6 i.

1S-2-Oxa-3-oxo-6R-(3R-hydroxy-4,4-propanooct-trans-1-enyl)-7R-hydroxy-cis-bicyclo[3,3,0]octane A heterogeneous mixture of 1S-2-oxa-3-oxo-6R-(3R-hydroxy-4,4-propanooct-trans-1-enyl)-7R-acetoxy-cis-bicyclo[3,3,0]octane (1.4 g., 4.00 mmol), prepared as described in Reference Example 5(i), finely powdered anhydrous potassium carbonate (0.555 g., 4.02 mmol), and methanol (12 ml.) was vigorously stirred at room temperature for 15 minutes and then cooled in an ice bath. After addition of1.0N hydrochloric acid (7.1 ml.), the reaction mixture was extracted with chloroform. The organic layer was washed with a saturated aqueous solution of sodium bicarbonate, dried over sodium sulphate, and concentrated by rotary evaporation to afford an oily product. The crude product was crystalized using diisopropyl ether to give 0.930 g. (yield 75%) of white crystals of the title compound having the following physical characteristics:-

NMR (CDCl$_3$): δ; 5.82-5.30 (2H, multiplet), 5.05-4.77 (1H, multiplet), 3.95 (1H, quartet, J=7.5 Hz) 3.96 (1H, doublet, J=7.0 Hz.), 0.92 (3H, triplet);
IR (CHCl$_3$): ν; 3400, 1770, 980 cm$^{-1}$;
Mass spectrum: m/e = 309 (M$^+$+1), 308 (M$^+$), 291 (M$^+$+1−18),
273 (M$^+$+1-36), 198 (M$^+$+1-111);
Optical rotation: [α]$_D^{23}$ = − 5.61° (C = 1.26, CHCl$_3$); m.p.: 110°-112° C.

ii 1S-2-Oxa-3-oxo-6R-(3R-hydroxy-4,4-propanooctyl)-7R-hydroxy-cis-bicyclo[3,3,0]octane Proceeding as described in Reference Example 6(i) using 720 mg. of 1S-2oxa-3-oxo-6R-(3R-hydroxy-4,4-propanooctyl)-7R-acetoxy-cis-bicyclo[3,3,0]octane, prepared as described in Reference Example 5(ii), there were obtained 633 mg. of the title compound is almost quantitative yield as white crystals, which were used in Example 8(ii) described hereinafter without recrystallization. The compound has the following physical characteristics:

NMR (CDCl$_3$: CD$_3$OD = 1:1): δ; 5.10−4.90 (1H, multiplet),
4.07−3.80 (1H, multiplet), 3.52−3.40 (1H, multiplet), 0.93 (3H, broad triplet);
IR (KBr disc): ν; 3450, 1730, 1215 cm$^{-1}$;
Mass spectrum: m/e = 310 (M$^+$), 292 (M$^{30}$−18), 199 (M$^{30}$ −111), 111;
Optical rotation: [α]$_D^{23}$ = − 7.03° (C = 1.19, CHCl$_3$).

iii.

1S-2-Oxa-3-oxo-6R-(3R-hydroxy-4,4-propanohept-trans-1-enyl)-7R-hydroxy-cis-bicyclo[3,3,0]octane Proceeding as described in Reference Example 6(i) usng 5.0 g. of 1S-2-oxa-3-oxo6R-(3R-hydroxy-4,4-propanohept-trans-1-enyl)-7R-acetoxy-cis-bicyclo[3,3,0]-octane, prepared as described in Reference Example 5(iii), there were obtained 4.3 g. (yield 98%) of the title compound as a pale yellow oil having the following physical characteristics:

NMR (CSCl$_3$): δ; 5.82−5.34 (2H, multiplet), 5.02−4.80
(1H, multiplet), 4.09−3.87 (2H, multiplet), 1.02−0.80 (3H, multiplet);
IR (CHCl$_3$): ν; 3400, 1770, 1170, 1045, 980 cm$^{-1}$;
Mass spectrum: m/e = 295 (M$^+$+1), 294 (M$^+$), 277 (M$^+$−17),
276 (M$^+$−18);
Optical rotation: [α]$_D^{17}$ = − 7.90° (C = 1.03, CHCl$_3$).

1S-2-Oxa-3-oxo-6R-(3R-hydroxy-4,4-propanonon-trans-1-enyl)-7R-hydroxy-cis-bicylo[3,3,0]octane Proceeding as described in Reference Example 6(i), using 1.12 g. of 1S-2-oxa-3-oxo-6R-(3R-hydroxy-4,4-propanonon-trans-1-enyl)-7R-acetoxy-cis-bicyclo-[3,3,0]octane, prepared as described in Reference Example 5(iv), there was obtained 770 mg. (yield 79.1%) of the title compound as white crystals having the following physical characteristics: m.p. 97.5°-98.0° C.;
NMR (CDCl$_3$): δ; 5.80−5.37 (2H, multiplet), 5.01−4.78

(1H, multiplet), 4.12−3.82 (2H, multiplet), 0.89 (3H, broad triplet);

IR (CHCl$_3$): ν; 3400, 1770, 980 cm$^{-1}$;

Mass spectrum: m/e = 323 (M$^+$−1), 322 (M$^+$), 305 (M$^{30}$−17), 304 (M$^{30}$ −18), 287 (M$^{30}$ −35);

Optical rotation: [α]$_D^{23}$ = − 5.55° (C = 2.09, CHCl$_3$).

v.

1S-2-Oxa-3-oxo-6R-(3R-hydroxy-4,4-propanodec-trans-1-enyl)-7R-hydroxy-cis-bicyclo[3,3,0]octane Proceeding as described in Reference Example 6(i) using 1.34 g. of 1S-2-oxa-3-oxo-6R-(3R-hydroxy-4,4-propanodec-trans-1-enyl)-7R-acetoxy-cis-bicyclo-[3,3,0]octane, prepared as described in Reference Example 5(v), there were obtained 939 mg. (yield 78%) of the title compound as white crystals having the following physical characteristics:

m.p. 97°-98° C.;

NMR (CDCl$_3$): δ; 5.80−5.34 (2H, multiplet), 5.00−4.80

(1H, multiplet), 4.08−3.70 (1H, multiplet), 3.95 (1H, doublet, J= 7.0 Hz), 3.70−3.65 (1H, D$_2$O exchanged), 2.90−2.70 (1H, D$_2$O exchanged), 2.90−2.15 (6H, multiplet), 2.08−1.55 (6H, multiplet, 1.50−1.13 (10H, multiplet, 0.89 (3H, broad triplet);

IR (CHCl$_3$): ν; 3400, 1770, 980 cm$^{-1}$;

Mass spectrum: m/e = 319, 318 (M$^+$ −18), 206, 181, 151, 150;

Optical rotation: [α]$_D^{17}$ = −0.0329° (C = 2.46, CHCl$_3$).

REFERENCE EXAMPLE 7

1S-2-Oxa-3-oxo-6R-(3S-hydroxy-4,4-propanooct-trans-1-enyl)-7R-hydroxy-cis-bicyclo[3,3,0]octane Proceeding as described in Reference Example 6(i) using 1S-2-oxa-3-oxo-6R-(3S-hydroxy-4,4-propanooct-trans-1-enyl)-7R-acetoxy-cis-bicyclo[3,3,0]octane, prepared as described in Reference Example 5(i), as starting material, the title compound was obtained as a pale yellow oil having the following physical characteristics:

NMR (CHCl$_3$): δ; 5.82−5.38 (2H, multiplet), 5.12−4.80

(2H, multiplet), 4.00 (1H, doublet, J=5.5Hz), 2.02 (3H, singlet), 0.91 (3H, triplet);

IR (CHCl$_3$): ν; 3500, 1780, 1745, 1250, 980 cm$^{-1}$;

Mass spectrum: m/e = 351 (M$^+$ +1) 350 (M$^+$), 273 (M$^+$ +1−78), 272 (M$^+$ −78);

Optical rotation: [α]$_D^{25}$ = − 24.2° (C = 2.41, CHCl$_3$).

REFERENCE EXAMPLE 8 i.

1S-2-Oxa-3-oxo-6R-(3R-2'-tetrahydropyranyloxy-4,4-propanooct-trans-1-enyl)-7R-2'-tetrahydropyranyloxy-cis-bicyclo[3,3,0]octane A solution of 1S-2-oxa-3-oxo-6R-(3R-hydroxy-4,4-propanooct-trans-1-eynl)-7R-hydroxy-cis-bicyclo-[3,3,0]octane (0.930 g.), prepared as described in Reference Example 6(i), p-toluenesulphonic acid (10 mg.) and freshly distilled 2,3-dihydropyran (3.0 ml.) in methylene chloride (11.0 ml.) was stirred for 15 minutes at room temperature. The reaction was quenched by addition of 7 drops of pyridine and the mixture diluted with chloroform. After washing with a saturated aqueous solution of sodium chloride, the organic layer was dried over sodium sulphate and concentrated to yield 1.7 g. (1.5 g. calculated; polymers derived from dihydropyran could be involved as impurity) of the title compound as a colourless oil. The crude product was used without purification in Reference Example 10(i) described hereinafter and has the following physical characteristics:

NMR (CDCl$_3$): δ; 5.85−5.18 (2H, multiplet), 5.18−4.78 1H, multiplet); 4.78−4.48 (2H, multiplet), 4.37−3.20 (6H, multiplet), 0.91 (3H, triplet);

IR (CHCl$_3$): ν; 1770, 1190, 1140, 1120, 1080, 1040, 1030, 980 cm$^{-1}$.

Mass spectrum: m/e = 420 (M$^+$ −56), 374 (M$^+$ −102), 365 (M$^+$ −111);

Optical rotation [α]$_D^{23}$ = − 35.1° (C = 1,36, CHCl$_3$).

ii.

1S-2-Oxa-3-oxo-6R-(3R-2'-tetrahydropyranyloxy-4,4-propanooctyl)-7R-2'-tetrahydropyranyloxy-cis-bicyclo-[3,3,0]octane Proceeding as described in Reference Example 8(i) using 606 mg. of 1S-2-oxa-3-oxo-6R-(3R-hydroxy-4,4-propanooctyl)-7R-hyddroxy-cis-bicyclo[3,3,0]octane, prepared as described in Reference Example 6ii, there were obtained 935 mg. (quantitative yield) of the title compound having the following physical characteristics:

NMR (CDCl$_3$): β; 5.07−4.86 (1H, multiplet), 470−4.43 (2H, multiplet), 4.15−3.70 (3H, multiplet), 3.60−3.30 (3H, multiplet), 0.91 (3H, broad triplet);

IR (CHCl$_3$): ν; 1770, 1140, 1080, 1030 cm$^{-1}$;

Mass spectrum: m/e = 395 (M$^+$ −83), 293, 283, 275 (M$^+$ −203), 199 (M$^+$ −279), 85;

Optical rotation: [α]$_D^{22}$ = − 0.143° (C = 1.86, CHCl$_3$).

iii.

1S-2-Oxa-3-oxo-6R-(3R-2'-tetrahydropyranyloxy-4,4-propanohept-trans-1-enyl)-7R-2'-tetrahydropyranyloxy-cis-bicyclo[3,3,0]octane Proceeding as described in Reference Example 8(i) using 3.70 g. of 1S-2-oxa-3-oxo-6R-(3R-hydroxy-4,4-propanohept-trans-1-enyl)-7R-hydroxy-cis-bicyclo-[3,3,0]octane, prepared as described in Reference Example 6(iii,) there was obtained a crude product which was partially purified by column chromatography on silica gel (110 g.) using a mixture of benzene and ethyl acetate (1:1) as eluant to yield the title compound (6.26 g.) as a pale yellow oil (containing a small amount of dihydropyran polymers having the following physical characteristics:

NMR (CDCl$_3$): δ; 5.70−5.35 (2H, multiplet), 5.10−4.80 (1H, multiplet), 4.78−4.52 (2H, multiplet), 4.25−3.26 (6H, multiplet), 0.89 (3H, broad triplet);

IR (CHCl$_3$): ν; 1770, 1140, 1080, 1030, 980 cm$^{-1}$;

Mass spectrum: m/e = 377 (M$^+$ −85), 360 (M$^+$ −102);

Optical rotation: [α]$_D^{18}$ = − 46.2° (C = 1.57, CHCl$_3$).

iv.

1S-2-Oxa-3-oxo-6R-(3R-2'-tetrahydropyranyloxy-4,4-propanoheptyl)-7R-2'-tetrahydropyranyloxy-cis-bicyclo[3,3,0]octane 700 mg. of 1S-2-oxa-3-oxo-6R-(3R-2'-tetrahydropyranyloxy-4,4-propanohept-trans-1enyl)-7R-2'-tetrahydropyranyloxy-cis-bicyclo[3,3,0]octane, prepared as described in Reference Example 8(iii,),in 20 ml. of methanol were subjected to catalytic hydrogenation in the presence of 250 mg. of 5% w/w palladium on carbon. After the reaction the catalyst was filtered off and the resulting filtrate evaporated to dryness under reduced pressure. The residue was etherified again by the conventional method (as described in Reference Example 8(i). According to the NMR spectrum the signal of hydrogen of a double bond near to $\delta = 5.50$ disappeared. 900 mg. (containing polymers of dihydropyran) of the title compound were obtained, as a yellow oil which was used without purification in Reference Example 10(iv) described hereinafter. The yellow oil has the following physical characteristics:

NMR (CDCl$_3$): $\delta$; 5.20–4.75 (2H, multiplet), 4.75–4.40 (3H, multiplet), 4.20–3.20 (6H, multiplet); 1.08–0.78 (3H, multiplet);

IR (liquid film): $\nu$; 1775, 1140, 1120, 1080, 1035 cm$^{-1}$.

v.

1S-2-Oxa-3-oxo-6R-(3R-2'-tetrahydropyranyloxy-4,4-propanonon-trans-1-enyl)-7R-2'-tetrahydropyranyloxy-cis-bicyclo[3,3,0]octane Proceeding as described in Reference Example (8i.) using 0.764 g. of 1S-2-oxa-3-oxo-6R-(3R-hydroxy-4,4-propanonon-trans-1-enyl)-7R-hydroxy-cis-bicyclo[3,3,0]octane, prepared as described in Reference Example 6(iv,) there were obtained 1.48 g. (containing a small amount of dihydpyran polymers) of the title compound as a yellow oil having the following physical characteristics:

NMR (CDCl$_3$): $\delta$; 5.58–5.35 (2H, multiplet), 5.04–4.82 (1H, multiplet), 4.74–4.65 (2H, multiplet), 0.89 (3H, broad triplet);

IR (CHCl$_3$): $\nu$; 1770, 1140, 1080, 1030, 980 cm$^{-1}$;

Mass spectrum: m/e = 388 (M$^+$ − 102), 366 (M$^+$ − 124), 305 (M$^+$31 185), 304 (M$^+$ − 186);

Optical rotation: $[\alpha]_D^{23}$ = − 22.4° (C = 2.91, CHCl$_3$).

vi.

1S-2-Oxa-3-oxo-6R-(3R-2'-tetrahydropyranyloxy-4,4-propanodec-trans-1-enyl)-7R-2'-tetrahydropyranyloxy-cis-bicyclo[3,3,0]octane Proceeding as described in Reference Example 8(i) using 939 mg. of 1S-2-oxa-3-oxo-6R-(3R-hydroxy-4,4-propanodec-trans-1-enyl)-7R-hydroxy-cis-bicyclo[3,3,0]octane, proceeding as described in Reference Example 6(v), the title compound was obtained in quantitative yield. It has the following physical characteristics:

NMR (CDCl$_3$): $\delta$; 5.60–5.34 (2H, multiplet), 5.10–4.80 (1H, multiplet), 4.75–4.55 (2H, multiplet), 4.20–3.70 (4H, multiplet), 3.62–3.30 (2H, multiplet), 1.40–1.10 (10H, multiplet), 0.89 (3H, broad triplet);

IR (CHCl$_3$): $\nu$; 1770, 1190, 1140, 1120, 1080, 1040, 1030, 980 cm$^{-1}$.

Mass spectrum: m/e = 420 (M$^+$ − 84), 403 (M$^+$ − 101), 365 (M$^+$ − 139), 319, 318 (M$^+$ − 186), 282, 281 (M$^+$ − 223), 85;

Optical rotation: $[\alpha]_D^{22}$ = − 19.8° (C = 0.550, CHCl$_3$).

REFERENCE EXAMPLE 9

1S-2-Oxa-3-oxo-6R-(3S-2'-tetrahydropyranyloxy-4,4-propanoct-trans-1-enyl)-7R-2'-tetrahydropyranyloxy-cis-bicyclo[3,3,0]octane Proceeding as described in Reference Example 8(i) using 1S-2-oxa-3-oxo-6R-(6S-hydroxy-4,4-propanoct-trans-1-enyl)-7R-hydroxy-cis-bicyclo[3,3,0]octane, prepared as described in Reference Example 7, the title compound was obtained as a yellow oil having the following physical characteristics:

NMR (CSCl$_3$): $\delta$; 5.62–5.30 (2H, multiplet), 5.10–4.78 (1H, multiplet), 4.75"4.50 (2H, multiplet), 4.20–3.30 (6H, multiplet), 0.91 (3H, triplet);

IR (CHCl$_3$): $\nu$; 1780, 1190, 1140, 1080, 1040, 1030, 980 cm$^{-1}$.

Mass spectrum: m/e = 374 (M$^+$ − 102);

Optical rotation: $[\alpha]_D^{24}$ = + 10.2° (C = 2.94, CHCl$_3$).

REFERENCE EXAMPLE 10 i.

1S-2-Oxa-3($\epsilon$)-hydroxy-6R-(3R-2'-tetrahydropyranyloxy-4,4-propanooct-trans-1-enyl)-7R-2'-tetrahydropyranyloxy-cis-bicyclo[3,3,0]octane To a stirred cold solution (−70° C.) of the crude 1S-2-oxa-3-oxo-6R-(3R-2'-tetrahydropyranyloxy-4,4-propanooct-trans-1-enyl)-7R-2'-tetrahydrapyranyloxy-cis-bicyclo[3,3,0]octane (0.415 g., 0.872 mmol), prepared as described in Reference Example 8(i,) in toluene (8.0 ml.) was added dropwise 2.0 ml. of a solution (25 g./100 ml.) in toluene of diisobutylaluminium hydride (0.500 g., 3.52 mmol.). The homogeneous solution was stirred for 20 minutes at −70° C., and then quenched by addition of methanol (5.0 ml.). After stirring for 15 minutes at room temperature, and then dilution with diethyl ether, the ethereal solution was washed with a saturated aqueous solution of sodium chloride. After removal of gelled substances by suction filtration through Celite 545, the ethereal solution was dried over magnesium sulphate and concentrated to yield the title compound which was used immediately without purification in Example 1 described hereinafter.

ii.

1S-2-Oxa-3($\epsilon$)-hydroxy-6R-(3R-2'-tetrahydropyranyloxy-4,4-propanooctyl)-7R-2'-tetrahydropyranyloxy-cis-bicyclo[3,3,0]octane Proceeding as described in Reference Example 10(i) using 863 mg. of 1S-2-oxa-3-oxo-6R-(3R-2'-tetrahydropyranyloxy-4,4-propanooctyl)-7R-2'-tetrahydropyranyloxy-cis-bicyclo[3,3,0]octane, prepared as described in Reference Example 8(ii,) the title compound was obtained in almost quantitative yield. iii. 1S-2-Oxa-3($\epsilon$)-hydroxy-6R-(3R-2'-tetrahydropyranyloxy-4,4-propanohept-trans-1-enyl)-7R-2'-tetrahydropyranyloxy-cis-bicyclo[3,3,0]octane Proceeding as described in Reference Example 10(i) using 1.36 g. of 1S-2-oxa-3-oxo-6R-(3R-2'-tetrahydropyranyloxy-4,4-propanohept-trans-1-enyl)-7R-2'-tetrahydropyranyloxy-cis-bicyclo[3,3,0]octane, prepared as described in Reference Example 8(iii), the title compound was obtained in almost quantitative yield as a pale yellow oil, which was used immediately without purification in Example 6 described hereinafter. iv. 1S-2-Oxa-3($\epsilon$)-hydoxy-6R-(3R-2'-tetrahydropyranyloxy-4,4-propanoheptyl)-7R-2'-tetrahydropyranyloxy-cis-bicyclo[3,3,0]octane Proceeding as described in Reference Example 10(i) using 1.40 g. of 1S-2-oxa-3-oxo-6R-(3R-2'-tetrahydropyranyloxy-4,4-propanoheptyl)-7R-2'-tetrahydropyranyloxy-cis-bicyclo[3,3,0]octane, prepared as described in Reference Example 8(iv,) there was obtained 1.27 g. (yield 90.3%) of the title compound having the following physical characteristics:

NMR (CDCl₃): δ; 5.70−5.38 (1H, multiplet), 4.77−4.51 (2H, multiplet), 4.13−3.38 (7H, multiplet), 1.02−0.80 (3H, multiplet);

IR (liquid film): ν; 3400, 1140, 1120, 1080, 1030 cm⁻¹.

v. 1S-2-Oxa-3(ε)-hydroxy-6R-(3R-2'-tetrahydropyranyloxy-4,4-propanonon-trans-1-enyl)-7R-2'-tetrahydropyranyloxy-cis-bicyclo[3,3,0]octane Proceeding as described in Reference Example 10(i) using 1.40 g. of 1S-2-oxa-3-oxo-6R-(3R-2'-tetrahydropyranyloxy-4,4-propanonon-trans-1-enyl)-7R-2'-tetrahydropyranyloxy-cis-bicyclo[3,3,0]octane, prepared as described in Reference Example 8(v), the title compound was obtained in almost quantitative yield as a pale yellow oil, which was used immediately in Example 10 described hereinafter. vi. 1S-2-Oxa-3(ε)-hydroxy-6R-3R-2'-tetrahydropyranyloxy-4,4-propanodec-trans-1-enyl)-7R-2'-tetrahydropyranyloxy-cis-bicyclo[3,3,0]octane Proceeding as described in Reference Example 10(i) using 1.30 g. of 1S-2-oxa-3-oxo-6R-(3R-2'-tetrahydropyranyloxy-4,4-propanodec-trans-1-enyl)-7R-2'-tetrahydropyranyloxy-cis-bicyclo[3,3,0]octane, prepared as described in Reference Example 8(vi), the title compound was obtained in almost quantitative yield.

REFERENCE EXAMPLE 11

1S-2-oxa-3(ε)-hyroxy-6R-(3S-2'-tetrahydropyranyloxy-4,4-propanooct-trans-1-enyl)-7R-2'-tetrahydropyranyloxy-cis-bicyclo[3,3,0]octane Proceeding as described in Reference Example 10(i) using 1S-2-oxa-3-oxo-6R-(3S-2'-tetrahydropyranyloxy-4,4-propanooct-trans-1-enyl)-7R-2'-tetrahydropyranyloxy-cis-bicyclo[3,3,0]octane, prepared as described in Reference Example 9, the title compound was obtained as a pale yellow oil.

EXAMPLE 1

9α-Hydroxy-11α,15R-bis-(2-tetrahydropyranyloxy)-16,16-propanoprosta-cis-5,trans-13-dienoic acid Sodiomethylsulphinylcarbanide was prepared as follows: A mixture of sodium hydride (242 mg.) and anhydrous dimethyl sulphoxide (5.0 ml.) was stirred at 60° C. until gas evolution ceased (ca. 2-3 hours). After cooling to room temperature, the solution was ready for use. The anhydrous dimethyl sulphoxide was prepared by drying and distilling over calcium hydride.

To a solution of 4-carboxy-n-butyl-triphenyl-phosphonium bromide in anhydrous dimethyl sulphoxide (3.0 ml.) was added 3.66 ml. (7.38 mmol) of sodiomethylsulphinylcarbanide with stirring to give a red solution, to which, after a further 5 minutes stirring, a solution of the 1S-2-oxa-3(ε)-hydroxy-6R-(3R-2'-tetrahydropyranyloxy-4,4-propanooct-trans-1-enyl)-7R-2'-tetrahydropyranyloxy-cis-bicyclo[3,3,0]octane, prepared in Reference Example 10(i), in dimethyl sulphoxide (3.0 ml.) was added. The reaction mixture was stirred at 25° C±1° for 2 hours, at 50° C. for an additional 30 minutes, and then quenched with ice-water. The reaction mixture was diluted with a mixture of ethyl acetate and diethyl ether (1:1), and then shaken with an aqueous solution of potassium carbonate, after which the pH of the solution was about 10. After confirming by TLC that no product was present in the organic layer, the aqueous layer was acidified to pH2-3 with 1.0N hydrochloric acid and extracted with a mixture of pentane and diethyl ether (1:1). The acidic extracts were dried over magnesium sulphate and concentrated to yield 711 mg. of oily product. The oily product was purified by preparative TLC [using as developing solvent a mixture of chloroform and methanol (20:2) and as eluant a mixture of chloroform and methanol (4:1)]to give 328 mg. (yield 67% based on 1S-2-oxa-3-oxo-6R-(3R-2'-tetrahydropyranyloxy-4,4-propanooct-trans-1-enyl)-7R-2'-tetrahydropyranyloxy-cis-bicyclo[3,3,0]octane) of the title compound as a pure oily product having the following physical characteristics:

NMR (CDCl₃): δ; 6.95−6.00 (2H, multiplet), 5.78−5.18 (4H, multiplet), 4.85−4.52 (2H, multiplet), 4.30−3.30 (7H, multiplet), 0.91 (3H, triplet);

IR (CHCl₃): ν; 3600−2300, 3500, 1715, 1140, 1120, 1080, 1040, 1025, 980 cm⁻¹;

Mass spectrum: m/e = 460 (M⁺−102), 358 (M⁺−204);

Optical rotation: $[\alpha]_D^{24}$ = +7.28° (C = 1.78, CHCl₃).

EXAMPLE 2

9α-Hydroxy-11α,15S-bis-(2-tetrahydropyranyloxy)-16,16-propanoprosta-cis-5,-trans-b 13-dienoic acid Proceeding as described in Example 1 using 1S-2-oxa-3(ε)hydroxy-6R-(3S-2'-tetrahydropyranyloxy-4,4-propanooct-trans-1-enyl)-7R-2'-tetrahydropyranyloxy-cis-bicyclo[3,3,0]octane, prepared as described in Reference Example 11, as starting material, the title compound was obtained as a yellow oil having the following physical characteristics:

NMR (CDCl₃): δ; 6.60−5.72 (2H, D₂O exchanged), 5.70−5.20 (4H, multiplet), 4.85−4.55 (2H, multiplet), 4.25−3.30 (7H, multiplet), 0.91 (3H, triplet);

IR (CHCl₃): ν; 3600−2300, 3500, 1710, 1140, 1120, 1080, 1040, 1030, 980 cm⁻¹;

Mass spectrum: m/e = 460 (M⁺−102), 376 (M⁺−186), 358 (M⁺−204);

Optical rotation: $[\alpha]_D^{20}$ = +40.1° (C=1.78, CHCl₃).

In a similar manner to that described in Reference Examples 5, 6, 7, 8, 9, 10, 11 and Examples 1 and 2, the following compounds may be prepared: 9α-hydroxy-11α,15R-bis-(2-tetrahydropyranyloxy)-16,18-methano-18-methyl-ω-nor-prosta-cis-5,trans-13-dienoic acid, 9α-hydroxy-11α,15R-bis-(2-tetrahydropyranyloxy)-16,17-ethano-16-phenyl-ω-trinor-prosta-cis-5,trans-13-dienoic acid, 9α-hydroxy-11α,15R-bis-(2-tetrahydropyranyloxy)-16,17-ethano-ω-dinor-prosta-cis-5,trans-13-dienoic acid and 9α-hydroxy-11α,15R-bis-(2-tetrahydropyranyloxy)-16,18-methano-ω-dihomo-prosta-cis-5,trans-13dienoic acid.

EXAMPLE 3

9α-Hydroxy-11α,15R-bis-(2-tetrahydropyranyloxy)-16,16-propanoprosta-cis-5-enoic acid Proceeding as described in Example 1 using 866 mg. of 1S-2-oxa-3(107)-hydroxy-6R-(3R-2'-tetrahydropyranyloxy-4,4-propanooctyl)-7R-2'-tetrahydropyranyloxy-cis-bicyclo[3,3,0]octane, prepared as described in Reference Example 10(ii), there were obtained 429 mg. (yield 42% based on 1S-2-oxa-6R-(3R-2'-tetrahydropyranyloxy-4,4-propanooctyl)-7R-2'-tetrahydropyranyloxy-cis-bicyclo[3,3,0]octane) of the title compound having the following physical characteristics:

NMR (CDCl₃): δ; 5.60−5.30 (2H, multiplet), 5.70−5.10 (2H, D₂O exchanged), 4.75−4,56 (2H, multiplet), 4.20−3.70 (4H, multiplet), 3.61−3.35 (3H, multiplet), 0.93 (3H, broad triplet);

IR (CHCl₃): ν; 3455, 3700−2300, 1710, 1130, 1115, 1075, 1020 cm⁻¹;

Optical rotation: $[\alpha]_D^{27}$ = +24.2° (C = 1.24, CHCl₃).

EXAMPLE 4

9α-Hydroxy-11α,15R-bis-(2-tetrahydropyranyloxy)-16,16-propanoprosta-trans-13-enoic acid 228 mg. of 9α-hydroxy-11α,15R-bis-(2-tetrahydropyranyloxy)-16,16-propanoprosta-cis-5, trans-13-dienoic acid (prepared as described in Example 1) in 5 ml. of methanol were subjected to catalytic hydrogenation in the presence of 76.0 mg. of 5% w/w palladium on carbon. Hyrdrogen was carried out at room temperature and atmospheric pressure until the starting material could not be detected by thin layer chromatography on a silica gel plate pre-treated with silver nitrate (a mixture of chloroform and methanol (20:1) was used as a developing solvent). After the reaction the catalyst was filtered off and the resulting filtrate evaporated to dryness under reduced pressure. Yield of the title compound was 197 mg. The NMR spectrum shows the absence of the signal due to two hydrogens of the cis-double bond near to δ = 5.50 ppm. The title compound has the following physical characteristics:

NMR (CDCl₃): δ; 6.70−6.40 (2H, D₂O exchanged), 5.70−5.30 (2H, multiplet), 4.90−4.55 (2H, multiplet), 4.30−3.20 (6H, multiplet);

IR (CHCl₃):ν; 3600−2300, 3400, 1710, 1120, 1080, 1025, 980 cm⁻¹.

EXAMPLE 5

9α-Hydroxy-11α,15R-bis-(2-tetrahydropyranyloxy)-16,16-propanoprostanoic acid 192 mg. of 9α-hydroxy-11α,15R-bis-(2-tetrahydropyranyloxy)-16,16-propanoprosta-cis-5,trans-13-dienoic acid (prepared as described in Example 1) in 10 ml. of methanol were subjected to catalytic hydrogenation in the presence of 64 mg. of 5% palladium on carbon water under a hydrogen atmosphere. After treatment overnight at room temperature the catalyst was filtered off and the resulting filtrate was evaporated to dryness under reduced pressure to yield 160 mg. of the title compound. The NMR spectrum shows the absence of signals due to two hydrogens of the double near to δ = 5.50 ppm. The title compound has the following physical characteristics:

NMR (CDCl₃): δ; 6.10−5.90 (2H, multiplet), 4.72−4.50 (2H, multiplet), 4.16−3.70 (4H, multiplet), 3.57−3.30 (3H, multiplet), 0.91 (3H, broad triplet);

IR (CHCl₃): ν; 3600−2300, 3500, 1710, 1140, 1120, 1080, 1030, 1005 cm⁻¹;

Mass spectrum: m/e=346 (M⁺−220), 271, 235, 85;

Optical rotation: $[\alpha]_D^{25}$ = +11.0° (C = 2.28, CHCl₃).

EXAMPLE 6

9α-Hydroxy-11α,15R-bis-(2-tetrahydropyranyloxy)-16,16-propano-ω-nor-prosta-cis-5,trans-13-dienoic acid Proceeding as described in Example 1 using 1.36 g. of 1S-2-oxa-3(ε)-hydroxy-6R (3R-2'-tetrahydropyranyloxy-4,4-propanohept-trans-1-enyl)-7R-2'-tetrahydropyranyloxy-cis-bicyclo[3,3,0]octane, prepared as described in Reference Example 10(iii), there were obtained 770 mg. (yield 46.8% based on 1S-2-oxa-3(ε)-hydroxy-6R-(3R-2'-tetrahydropyranyloxy-4,4-propanohept-trans-1-enyl)-7R-2'-tetrahydropyranyloxy-cis-bicyclo[3,3,0]octane) of the title compound having the following physical characteristics:

NMR (CDCl₃); δ; 5.65−5.26 (4H, multiplet), 4.76−4.54 (2H, multiplet), 4.20−3.66 (4H, multiplet), 3.60−3.43 (2H, multiplet), 0.98−0.76 (3H, multiplet);

IR (CHCl₃): ν; 3600−2400, 1715, 1140, 1120, 1080, 1030, 980 cm⁻¹;

Mass spectrum: m/e = 446 (M⁺−102), 344 (M⁺−204).

EXAMPLE 7

9α-Hydroxy-11α,15R-bis-(2-tetrahydropyranyloxy)-16,16-propano-ω-nor-prosta-cis-5-enoic acid Proceeding as described in Example 1 using 840 mg. of 1S-2-oxa-3(ε)-hydroxy-6R-(3R-2'-tetrahydropyranyloxy-4,4-propanoheptyl)-7R-2'-tetrahydropyranyloxy-cis-bicyclo[3,3,0]octane, prepared as described in Reference Example 10(iv), there were obtained 589 mg. (yield 58%) of the title compound having the following physical characteristics:

NMR (CDCl₃): δ; 5.70−5.30 (2H, multiplet), 4.75−4.22 (4H, multiplet, two of them were D₂O exchanged), 4.19−3.65 (2H, multiplet), 3.63−3.34 (2H, multiplet), 1.02−0.81 (3H, multiplet);

IR (CHCl₃): ν; 3600−2400, 1710, 1140, 1120, 1080, 1030;

Mass spectrum: m/e=466 (M⁺−84), 465 (M⁺−85), 448 (M⁺−102), 346 (M⁺−204).

EXAMPLE 8

9α-Hydroxy-11α,15R-bis-(2-tetrahydropyranyloxy)-16,16-propano-ω-nor-prostanoic acid Proceeding as described in Example 5 using 380 mg. of 9α-hydroxy-11α,15R-bis-(2-tetrahydropyranyloxy)-16,16-propano-ω-nor-prosta-cis-5,trans-13-dienoic acid, prepared as described in Example 6, there were obtained 371 mg. (yield 96.8%) of the title compound having the following physical characteristics:

NMR (CDCl₃): δ; 6.02−5.72 (2H, multiplet), 4.77−4.46 (2H, multiplet), 4.20−3.66 (4H, multiplet), 3.62−3.30 (2H, multiplet), 1.03−0.80 (3H, multiplet);

IR (CHCl₃): ν; 3600−2400, 1710, 1130, 1110, 1080, 1030 cm⁻¹.

EXAMPLE 9

9α-Hydroxy-11α,15R-bis-(2-tetrahydropyranyloxy)-16,16-propano-ω-nor-prostanoic acid methyl ester Proceeding as described in Example 37 described hereinafter using 335 mg. of 9α-hydroxy-11α,15R-bis-(2-tetrahydropyranyloxy)-16,16-propano-ω-nor-prostanoic acid, prepared as described in Example 8, there were obtained 330 mg. (yield 96.2%) of the title compound having the following physical characteristics:-

NMR (CDCl₃): δ; 4.76−4.53 (2H, multiplet), 4.19−3.34 (7H, multiplet), 3.67 (3H, singlet), 2.31 (2H, triplet, J=7.0 Hz), 1.03−0.80 (3H, multiplet);

IR (CHCl₃): ν; 3500, 1735, 1130, 1115, 1080, 1030 cm⁻¹;

Mass spectrum: m/e = 481 (M⁺−85), 469 (M⁺−97), 464 (M⁺−102), 463 (M⁺−103), 385 (M⁺−181).

EXAMPLE 10

9α-Hydroxy-11α,15R-bis-(2-tetrahydropyranyloxy)-16,16-propano-ω-homo-prosta-cis-5,trans-13-dienoic acid Proceeding as described in Example 1 using 1.40 g. (containing polymers of dihydropyran) of 1S-2-oxa-3(ε)-hydroxy-6R-(3R-2'-tetrahydropyranyloxy-4,4-propanonon-trans-1-enyl)-7R-2'-tetrahydropyranyloxy-cis-bicyclo[3,3,0]octane, prepared as described in Reference Example 10(v), there were obtained 777 mg. (yield 59% based on 1S-2-oxa-3-oxo-6R-(3R-hydroxy-4,4-propanonon-trans-1-enyl)-7R-hydroxy-cis-bicyclo[3,3,0]-octane) of the title compound having the following physical characteristics:-

NMR (CDCl$_3$): δ; 5.69−5.10 (6H, multiplet), 4.55−4.72 (2H, multiplet), 4.22−3.30 (7H, multiplet), 0.88 (3H broad triplet);

IR (CHCl$_3$): ν; 3600−2400, 1710, 1130, 1115, 1075, 1020, 975 cm$^{-1}$;

Mass spectrum: m/e = 474 (M$^+$−102), 372 (M$^+$−204).

EXAMPLE 11

9α-Hydroxy-11α,15R-bis-(2-tetrahydropyranyloxy)-16,16-propano-ω-dihomo-prosta-cis-5,trans-13-dienoic acid Proceeding as described in Example 1 using 1.30 g. of 1S-2-oxa-3(ε)-hydroxy-6R-(3R-2'-tetrahydropyranyloxy-4,4-propanodec-trans-1-enyl)-7R-2'-tetrahydropyranyloxy-cis-bicyclo[3,3,0]octane, prepared as described in Reference Example 10(vi), there were obtained 511 mg. (yield 34% based on 1S-2-oxa-3-oxo-6R-(3R-2'-tetrahydropyranyloxy-4,4-propanodec-trans-1-enyl)-7R-2'-tetrahydropyranyloxy-cis-bicyclo[3,3,0]-octane) of the title compound (827 mg. of the starting material were recovered) having the following physical characteristics:-

NMR (CDCl$_3$): δ; 5.70−5.25 (2H, multiplet), 4.80−4.60 (2H, multiplet), 4.30−3.65 (4H, multiplet), 4.50−4.20 (2H, D$_2$O exchanged), 3.60−3.30 (2H, multiplet), 1.35−1.10 (10H, multiplet), 0.88 (3H, broad triplet);

IR (CHCl$_3$): ν; 3600−2300, 3500, 1710, 1140, 1120, 1080, 1040, 1025, 980 cm$^{-1}$;

Mass spectrum: m/e = 405 (M$^+$−185), 388, 334, 304, 285, 250, 201, 85;

Optical rotation: [α]$_D^{18}$ = −11.8° (C = 2.47, CHCl$_3$).

EXAMPLE 12

9-Oxo-11α,15R-bis-(2-tetrahydropyranyloxy)-16,16-propanoprosta-cis-5,trans-13-dienoic acid A solution of manganese sulphate (5.7 g.) in water (28 ml.) was treated with 1.36 ml. of concentrated sulphuric acid followed by chromium trioxide (1.24 g.) at 0° C. After stirring for 5 minutes at 0° C., the solution of oxidizing agent was ready for use.

To a solution of 9α-hydroxy-11α,15R-bis-(2-tetrahydropyranyloxy)-16,16-propanoprosta-cis-5,trans-13-dienoic acid, prepared as described in Example 1, in diethyl ether (2.0 ml.) was added the previously prepared oxidizing agent at 0° C. After stirring for 2.5 hours at 0° C. the two phase reaction mixture was diluted with ethyl acetate. The organic layer was washed with a saturated aqueous solution of sodium chloride, dried over magnesium sulphate and concentrated to yield an oily product. The product was purified by column chromatography on silica gel (23 g.) using a mixture of methylene chloride and methanol (20:1) as eluant to give 385 mg. (yield 84%) of the title product having the following physical characteristics:-

NMR (CDCl$_3$): δ; 9.60 −8.90 (1H, multiplet), 5.75−5.45 (2H, multiplet), 5.50−5.30 (2H, multiplet), 4.86−4.47 (2H, multiplet), 4.40−3.27 (6H, multiplet), 0.92 (3H, triplet);

IR (CHCl$_3$): ν; 3600−2400, 1745, 1715, 1140, 1080, 1040, 1030, 980 cm$^{-1}$;

Mass spectrum: m/e = 458 (M$^+$−102), 374 (M$^+$−186), 356 (M$^+$−204);

Optical rotation: [α]$_D^{25}$ = −65.9° (C = 2.19, CHCl$_3$).

EXAMPLE 13

9-Oxo-11α,15S-bis-(2-tetrahydropyranyloxy)-16,16-propanoprosta-cis-5,trans-13-dienoic acid Proceeding as described in Example 12 using 9α-hydroxy-11α,15S-bis-(2-tetrahydropyranyloxy)-16,16-propanoprosta-cis-5,trans-13-dienoic acid, prepared as described in Example 2, the title compound was obtained as a pale yellow oil having the following physical characteristics:-

NMR (CDCl$_3$): δ; 8.90−8.80 (1H, multiplet), 5.80−5.20 (4H, multiplet), 4.80−4.55 (2H, multiplet), 4.30−3.30 (6H, multiplet), 0.93 (3H, multiplet); (6H, multiplet), 0.93 (3H, triplet);

IR (CHCl$_3$): ν; 3600−2300, 1750, 1720, 1140, 1080, 1040, 1030, 980 cm$^{-1}$;

Optical rotation: [α]$_D^{25}$ = −30.8° (C = 2.97, CHCl$_3$).

EXAMPLE 14

9-Oxo-11α,15R-bis-(2-tetrahydropyranyloxy)-16,16-propanoprosta-cis-5-enoic acid

Proceeding as described in Example 12 using 389 mg. of 9α-hydroxy-11α,15R-bis-(2-tetrahydropyranyloxy)-16,16-propanoprosta-cis-5-enoic acid, prepared as described in Example 3, 266 mg. (yield 69%) of the title compound were obtained having the following physical characteristics:-

NMR (CDCL$_3$): δ; 7.50−6.80 (1H, D$_2$O exchanged), 5.50−5.30 (2H, multiplet), 4.78−4.52 (2H, multiplet), 4.30−3.70 (3H, multiplet), 3.65−3.35 (3H, multiplet), 0.93 (3H, broad triplet);

IR (CHCl$_3$): ν; 3600−2300, 1740, 1710, 1130, 1080, 1025 cm$^{-1}$;

Mass spectrum: m/e = 376, 359, 358 (M$^+$−204), 341 (359−18), 265, 247, 85;

Optical rotation: [α]$_D^{26}$ = −21.1° (C = 2.20, CHCl$_3$).

EXAMPLE 15

9-Oxo-11α,15R-bis-(2-tetrahydropyranyloxy)-16,16-propanoprosta-trans-13-enoic acid Proceeding as described in Example 12 using 197 mg. of 9α-hydroxy-11α,15R-bis-(2-tetrahydropyranyloxy)-16,16-propanoprost-trans-13-enoic acid, prepared as described in Example 4, 152 mg. (yield 77%) of the title compound were obtained having the following physical characteristics:-

IR (CHCl$_3$): ν; 3600−2300, 1740, 1710, 1135, 1080, 1035, 1025, 980 cm$^{-1}$;

Optical rotation: [α]$_D^{27}$ = −56.5° (C = 1.61, CHCl$_3$).

EXAMPLE 16

9-Oxo-11α,15R-bis(2-tetrahydropyranyloxy)-16,16-propanoprostanoic acid

Proceeding as described in Example 12 using 160 mg. of 9α-hydroxy-11α,15R-bis-(2-tetrahydropyranyloxy)-16,16-propanoprostanoic acid, prepared as described in Example 5, 100 mg. (yield 63%) of the title compound were obtained having the following physical characteristics:-

NMR (CDCl$_3$): δ; 4.85–4.50 (2H, multiplet), 4.30–3.20 (6H, multiplet), 0.92 (3H, broad triplet);
IR (CHCl$_3$): ν; 3600–2300, 1740, 1710, 1140, 1080, 1030 cm$^{-1}$.

EXAMPLE 17

9-Oxo-11α,15R-bis-(2-tetrahydropyranyloxy)-16,16-propano-ω-nor-prosta-cis-5,trans-13-dienoic acid Proceeding as described in Example 12 using 668 mg. of 9α-hydroxy-11α,15R-bis-(2-tetrahydropyranyloxy)-16,16-propano-ω-nor-prosta-cis-5,trans-13-dienoic acid, prepared as described in Example 6, 650 mg. (yield 98%) of the title compound were obtained having the following physical characteristics:-

NMR (CDCl$_3$): δ; 9.50–8.50 (1H, D$_2$O exchanged), 5.75–5.25 (4H, multiplet), 4.83–4.55 (2H, multiplet), 4.30–3.65 (4H, multiplet), 3.60–3.30 (2H, multiplet), 0.95–0.75 (3H, multiplet);
IR (CHCl$_3$): ν; 3600–2300, 1740, 1710, 1140, 1080, 1040, 1030, 980 cm$^{-1}$;
Mass spectrum: m/e = 362, 361, 344 (M$^+$ –202), 264, 263, 85;
Optical rotation: [α]$_D^{23}$ = + 94.6° (C = 1.44, CHCl$_3$).

EXAMPLE 18

9-Oxo-11α,15R-bis-(2-tetrahydropyranyloxy)-16,16-propano-ω-nor-prosta-cis-5-enoic acid Proceeding as described in Example 12 using 344 mg. of 9α-hydroxy-11α,15R-bis-(2-tetrahydropyranyloxy)-16,16-propano-ω-nor-prosta-cis-5-enoic acid, prepared as described in Example 7, 270 mg. (yield 78.8%) of the title compound were obtained having the following physical characteristics:-

NMR (CDCl$_3$): δ; 6.70–6.22 (1H, multiplet), 5.51–5.40 (2H, multiplet), 4.75–4.52 (2H, multiplet), 4.26–3.32 (6H, multiplet), 1.02–0.83 (3H, multiplet);
IR (liquid film): ν; 3600–2400, 1745, 1710, 1135, 1080, 1030, 1020 cm$^{-1}$.

EXAMPLE 19

9-Oxo-11α,15R-bis-(2-tetrahydropyranyloxy)-16,16-propano-ω-nor-prostanoic acid

Proceeding as described in Example 12 using 370 mg. of 9α-hydroxy-11α,15R-bis-(2-tetrahydropyranyloxy)-16,16-propano-ω-nor-prostanoic acid, prepared as described in Example 8, 280 mg. (yield 76.0%) of the title compound were obtained having the following physical characteristics:- IR (liquid film): ν; 3600–2300; 1745, 1710, 1130, 1080, 1030 cm$^{-1}$.

EXAMPLE 20

9-Oxo-11α,15R-bis-(2-tetrahydropyranyloxy)-16,16-propano-ω-nor-prostanoic acid methyl ester Proceeding as described in Example 12 using 330 mg. of 9α-hydroxy-11α,15R-bis-(2-tetrahydropyranyloxy)-16,16-propano-ω-nor-prostanoic acid methyl ester, prepared as described in Example 9, 236 mg. (yield 71.8%) of the title compound were obtained having the following physical characteristics:-

NMR (CDCl$_3$): δ; 4.74–4.52 (2H, multiplet), 4.19–3.34 (6H, multiplet), 3.68 (3H, singlet), 2.31 (2H, triplet, J= 7.0 Hz), 1.04–0.81 (3H, multiplet);
IR (CHCl$_3$): ν; 1735, 1130, 1080, 1030 cm$^{-1}$;
Mass spectrum: m/e = 480 (M$^+$ –84), 479 (M$^+$ –85), 463 (M$^+$ –101), 462 (M$^+$ –102), 393 (M$^+$ –171), 389 (M$^+$ –175).

EXAMPLE 21

9-Oxo-11α,15R-bis-(2-tetrahydropyranyloxy)-16,16-propano-ω-homo-prosta-cis-5,trans-13-dienoic acid Proceeding as described in Example 12 using 757 mg. of 9α-hydroxy-11α,15R-bis-(2-tetrahydropyranyloxy)-16,16-propano-ω-homo-prosta-cis-5,trans-13-dienoic acid, prepared as described in Example 10, 516 mg. (yield 68%) of the title compound were obtained having the following physical characteristics:-

NMR (CDCl$_3$): δ; 9.10–8.60 (1H, multiplet), 5.78–5.50 (2H, multiplet), 5.50–5.34 (2H, multiplet), 4.86–4.58 (2H, multiplet), 4.05–3.65 (4H, multiplet), 0.90 (3H, broad triplet);
IR (CHCl$_3$): ν; 3600–2400, 1745, 1715, 1135, 1080, 1030, 980 cm$^{-1}$;
Mass spectrum: m/e = 387 (M$^+$ –187), 369 (M$^+$ –205), 263 (M$^+$ –311).

EXAMPLE 22

9-Oxo-11α,15R-bis-(2-tetrahydropyranyloxy)-16,16-propano-ω-dihomo-prosta-cis-5,trans-13-dienoic acid Proceeding as described in Example 12 using 511 mg. of 9α-hydroxy-11α,15R-bis-(2-tetrahydropyranyl-oxy)-16,16-propano-ω-dihomo-prosta-cis-5,trans-13-dienoic acid, prepared as described in Example 11, 313 mg. (yield 61%) of the title compound were obtained having the following physical characteristics:-

NMR (CDCl$_3$): δ; 9.00–8.00 (1H, D$_2$O exchanged), 5.75–5.25 (4H, multiplet), 4.85–4.55 (2H, multiplet), 4.05–3.70 (4H, multiplet), 1.36–1.19 (10H, multiplet), 0.89 (3H, broad triplet);
IR (CHCl$_3$): ν; 3600–2300, 1740, 1710, 1140, 1120, 1080, 1040, 1025, 980 cm$^{-1}$;
Mass spectrum: m/e = 486, 485 (M$^+$ –103), 402 (M$^+$ –186), 385 (M$^+$ –203), 384, 318, 264, 263 (M$^+$ –325), 245, 85;
Optical rotation: [α]$_D^{20}$ = – 65.5° (C = 1.04, CHCl$_3$).

EXAMPLE 23

16,16-Propano-PGF$_{2\alpha}$

A solution of 9α-hydroxy-11α,15R-bis-(2-tetrahydropyranyloxy)-16,16-propanoprosta-cis-5,trans-13-dienoic acid (88 mg.), prepared as described in Example 1, in methanol (1.0 ml.) was treated with excess diazomethane in diethyl ether. After a few minutes, the reaction mixture was concentrated at room temperature, and dried sufficiently in vacuo to yield the crude methyl ester of 9α-hydroxy-11α,15R-bis-(2-tetrahydropyranyloxy)-16,16-propanoprosta-cis-5,trans-13-dienoic acid, which was used for the next reaction without purification.

A solution of the methyl ester obtained as described above and anhydrous p-toluenesulphonic acid (5 mg.) in absolute methanol (3.0 ml.) was stirred at room temperature for 2 hours. The mixture was treated with 1N aqueous sodium hydroxide and stirred for a further 1 hour. The reaction mixture was then acidified with 1N hydrochloric acid and extracted with methylene chloride. The extract was dried over sodium sulphate and concentrated to yield 100 mg. of oily product. The crude oily product was purified by preparative TLC [using as developing solvent a mixture of chloroform and methanol (20:2) and as eluant a mixture of chloroform and methanol (4:1)] to give 40 mg. (yield 65%) of pure 16,16-propano-PGF$_{2\alpha}$ having the following physical characteristics:-

NMR (CDCl$_3$): δ; 5.57−5.45 (2H, multiplet), 5.00−5.30 (2H, multiplet), 5.70−4.70 (4H, D$_2$O exchanged), 4.35−3.56

(3H, multiplet), 0.91 (3H, triplet);

IR (CHCl$_3$): ν; 3700−2300, 3375, 1715, 980 cm$^{-1}$;

Mass spectrum: m/e = 376 (M$^+$ − 18), 358 (M$^+$ − 36), 340

(M$^+$ − 54);

Optical rotation: [α]$_D^{23}$ = + 33.1° (C = 2.16, CHCl$_3$).

In a similar manner to that described in Example 23, there may be prepared 16,18-methano-18-methyl-ω-nor-PGF$_{2\alpha}$, 16,17-ethano-16-phenyl-ω-trinor-PGF$_{2\alpha}$, 16,17-ethano-ω-dinor-PGF$_{2\alpha}$ and 16,18-methano-ω-dihomo-PGF$_{2\alpha}$.

EXAMPLE 24

16,16-Propano-15-epi-PGF$_{2\alpha}$

Proceeding as described in Example 23 using 9α-hydroxy-11α,15S-bis-(2-tetrahydropyranyloxy)-16,16-propanoprosta-cis-5,trans-13-dienoic acid, prepared as described in Example 2, the title compound was obtained as a pale yellow oil having the following physical characteristics:-

TLC (developing solvent chloroform: methanol = 20:3) : Rf − 0.61;

NMR (CDCl$_3$): δ; 5.70−5.35 (4H, multiplet), 4.90−4.00

(4H, D$_2$O exchanged), 4.15−3.90 (3H, multiplet), 0.91

(3H, triplet);

IR (CHCl$_3$): ν; 3700−2300, 3400, 1715, 980 cm$^{-1}$;

Optical rotation: [α]$_D^{24}$ = + 8.12° (C = 0.825, CHCl$_3$).

EXAMPLE 25

16,16-Propano-ω-nor-13,14-dihydro PGF$_{1\alpha}$ methyl ester 130 mg. of 9α-hydroxy-11α,15R-bis-(2-tetrahydropyranyloxy)-16,16-propano-ω-nor-prosta-cis-5,trans-13-dienoic acid (prepared as described in Example 6) in 10 ml. of methanol were subjected to catalytic hydrogenation in the presence of 5% w/w palladium on carbon. Catalytic reduction of the starting material was carried out overnight at room temperature and atmospheric pressure. When no other compound than the required title compound could be detected on a silica gel plate pre-treated with silver nitrate [using as developing solvent a mixture of chloroform and methanol (20:1)], the reaction was terminated and the catalyst was removed by filtration. The filtrate was concentrated under reduced pressure. 860 mg. (yield 91.2%) of the title compound were obtained as a pale yellow oil, having the following physical characteristics:-

NMR (CDCl$_3$): δ; 4.21−4.09 (1H, multiplet), 4.02−3.89

(1H, multiplet), 3.65 (3H, singlet), 3.58−3.44 (1H, multiplet), 2.90−2.60 (3H, D$_2$O exchanged), 0.92 (3H, broad triplet);

IR (CHCl$_3$): ν; 3400, 1735 cm$^{-1}$;

Mass spectrum: m/e = 399 (M$^+$ + 1), 380 (M$^+$ − 18), 362 (M$^+$ − 36).

EXAMPLE 26

16,16-Propano-PGE$_2$

A mixture of crude 9-oxo-11α,15R-bis-(2-tetrahydropyranyloxy)-16,16-propanoprosta-cis-5,trans-13-dienoic acid (210 mg.), prepared as described in Example 12, 7.5 ml. of aqueous acetic acid (65% v/v) and THF (0.7 ml.) was stirred at 37° C. for 2.5 hours. The mixture was concentrated using a rotary evaporator to give an oil containing acetic acid which was removed azeotropically with toluene under reduced pressure. The residue was purified by preparative TLC [using as developing solvent a mixture of chloroform and ethanol (20:3) and as eluant a mixture of chloroform and methanol (4:1)] to give 82 mg. (yield 56%) of pure 16,16-propano-PGE$_2$ having the following physical characteristics:-

NMR (CDCl$_3$): δ; 6.00−5.00 (3H, D$_2$O exchanged), 5.74−5.52

(2H, multiplet), 5.00−5.28 (2H, multiplet), 4.50−3.60 (2H, multiplet), 0.93 (3H, triplet);

IR (CHCl$_3$); ν; 3600−2300, 3400, 1750, 1715, 980 cm$^{-1}$;

Mass spectrum: m/e = 374 (M$^+$ − 18), 356 (M$^+$ − 36);

Optical rotation: [α]$_D^{20}$ = − 55.3° (C = 4.08, CHCl$_3$).

In a similar manner to that described in Examples 12 and 26 there may be prepared 16,18-methano-18-methyl-ω-nor-PGE$_2$, 16,17-ethano-16-phenyl-ω-trinor-PGE$_2$, 16,17-ethano-ω-dinor-PGE$_2$, and 16,18-methano-ω-dihomo-PGE$_2$.

EXAMPLE 27

16,16-Propano-15-epi-PGE$_2$

Proceeding as described in Example 26 using 9-oxo-11α,15S-bis-(2-tetrahydropyranyloxy)-16,16-propanoprosta-cis-5,trans-13-dienoic acid, prepared as described in Example 13, the title compound was obtained as a pale yellow oil having the following physical characteristics:-

TLC (developing solvent chloroform:ethanol = 20:1, three developments): Rf = 0.57;

NMR (CDCl$_3$): δ; 5.82–5.60 (2H, multiplet), 5.55–5.30

(2H, multiplet), 5.70–4.70 (3H, D$_2$O exchanged), 4.25–3.90

(2H, multiplet), 0.93 (3H, triplet);

IR (CHCl$_3$): ν; 3600–2300, 3400, 1745, 1715, 980 cm$^{-1}$;

Mass spectrum: m/e = 374 (M$^+$ − 18), 356 (M$^+$ − 36);

Optical rotation: $[\alpha]_D^{18}$ = − 79.2° (C = 1.29, CHCl$_3$).

EXAMPLE 28

16,16-Propano-13,14-dihydro-PGE$_2$

Proceeding as described in Example 26 using 265 mg. of 9-oxo-11α,15R-bis-(2-tetrahydropyranyloxy)-16,16-propanoprosta-cis-5-enoic acid, prepared as described in Example 14, 130 mg. (yield 70%) of the title compound were obtained having the following physical characteristics:-

TLC (developing solvent chloroform:methanol = 20:2): Rf=0.32;

NMR (CDCl$_3$): δ; 5.50–5.30 (2H, multiplet), 6.50–5.54

(3H, D$_2$O exchanged), 4.30–4.00 (1H, multiplet), 3.70–3.40

(1H, multiplet), 0.92 (3H, broad triplet);

IR (CHCl$_3$): ν; 3700–2300, 3400, 1740, 1710 cm$^{-1}$;

Mass spectrum: m/e = 377, 376 (M$^+$ − 18), 359, 358 (M$^+$ − 36), 265, 247;

Optical rotation: $[\alpha]_D^{27}$ = − 31.7° (C = 1.13, CHCl$_3$).

EXAMPLE 29

16,16-Propano-PGE$_1$

Proceeding as described in Example 26 using 235 mg. of 9-oxo-11α,15R-bis-(2-tetrahydropyranyloxy)-16,16-propanoprosta-trans-13-enoic acid, prepared as described in Example 15, 98 mg. (yield 60%) of the title compound were obtained having the following physical characteristics:-

TLC (developing solvent chloroform:methanol = 20:2): Rf=0.38;

NMR (CDCl$_3$): δ; 5.80–5.50 (2H, multiplet), 5.80–5.20

(3H, D$_2$O exchanged), 4.20–3.80 (2H, multiplet), 0.89

(3H, broad triplet);

IR (CHCl$_3$): ν; 3600–2300, 3400, 1740, 1710 cm$^{-1}$;

Optical rotation: $[\alpha]_D^{27}$ = − 60.5° (C = 2.75, CHCl$_3$).

EXAMPLE 30

16,16-Propano-13,14-dihydro-PGE$_1$

Proceeding as described in Example 26 using 100 mg. of 9-oxo-11α,15R-bis-(tetrahydropyranyloxy)-16,16-propanoprostanoic acid, prepared as described in Example 16, 46 mg. (yield 66%) of the title compound were obtained having the following physical characteristics:-

TLC (developing solvent chloroform:methanol = 20:2): Rf=0.45;

NMR (CDCl$_3$): δ; 5.60–5.10 (3H, D$_2$O exchanged), 4.30–4.00 (1H, multiplet), 3.70–3.45 (1H, multiplet), 0.89 (3H broad triplet);

IR (CHCl$_3$): ν; 3700–2300, 3400, 1740, 1710 cm$^{-1}$;

Optical rotation: $[\alpha]_D^{25}$ = − 29.6° (C = 2.22, CHCl$_3$).

EXAMPLE 31

16,16-Propano-ω-nor-PGE$_2$

Proceeding as described in Example 26 using 631 mg. of 9-oxo-11α,15R-bis-(2-tetrahydropyranyloxy)-16,16-propano-ω-nor-prosta-cis-5,trans-13-dienoic acid, prepared as described in Example 17, 291 mg. (yield 66%) of the title compound were obtained having the following physical characteristics:-

TLC (developing solvent chloroform:methanol = 20:2): Rf=0.30;

NMR (CDCl$_3$): δ; 6.40–5.75 (3H, D$_2$O exchanged), 5.73–5.50 (2H, multiplet), 5.45–5.25 (2H, multiplet), 4.20–3.35 (2H, multiplet), 1.00–0.80 (3H, multiplet);

IR (CHCl$_3$): ν; 3700–2300, 3400, 1740, 1710, 980 cm$^{-1}$;

Mass spectrum: m/e = 360 (M$^+$ − 18), 342 (M$^+$ − 36), 264, 263 (M$^+$ − 115), 246;

Optical rotation: $[\alpha]_D^{28}$ = − 56.0° (C = 1.72, CHCl$_3$).

EXAMPLE 32

16,16-Propano-ω-nor-13,14-dihydro-PGE$_2$

Proceeding as described in Example 26 using 260 mg. of 9-oxo-11α,15R-bis-(2-tetrahydropyranyloxy)-16,16-propano-ω-prosta-cis-5-enoic acid, prepared as described in Example 18, 152 mg. (yield 84.3%) of the titel compound were obtained having the following physical characteristics:-

TLC (developing solvent chloroform:methanol = 10:1): Rf=0.28;

NMR (CDCl$_3$): δ; 5.52–5.30 (2H, multiplet), 5.23–4.98 (3H, multiplet), 4.28–3.97 (1H, multiplet), 3.66–3.45 (1H, multiplet), 1.04–0.81 (3H, multiplet);

IR (CHCl$_3$): ν; 3600–2400, 1740, 1710, 1240, 1050;

Mass spectrum: m/e = 373 (M$^+$ − 17), 372 (M$^+$ − 18), 345 (M$^+$ − 35), 344 (M$^+$ − 36).

EXAMPLE 33

16,16-Propano-ω-nor-13,14-dihydro-PGE$_1$

Proceeding as described in Example 26 using 248 mg. of 9-oxo-11α, 15R-bis-(2-tetrahydropyranyloxy)-16,16-propano-ω-nor-prostanoic acid, prepared as described in Example 19, 131 mg. (yield 76%) of the title compound were obtained having the following physical characteristics:

NMR (CDCl$_3$): δ; 5.80–5.10 (3H, multiplet), 4.28–3.94 (1H, multiplet), 3.65–3.40 (1H, multiplet), 1.10–0.80 (3H, multiplet);

IR (CHCl$_3$): ν; 3600–2300, 1740, 1715 cm$^{-1}$;

Mass spectrum: m/e = 375 (M$^+$ − 17), 374 (M$^+$ − 18), 347 (M$^+$ − 35), 346 (M$^+$ − 46).

EXAMPLE 34

16,16-Propano-ω-nor-13,14-dihydro-PGE$_1$ methyl ester

Proceeding as described in Example 26 using 236 mg. of 9-oxo-11α, 15R-bis-(2-tetrahydropyranyloxy)-16,16-propano-107 -nor-prostanoic acid methyl ester, prepared as described in Example 20, 140 mg. (yield 84.5%) of the title compound were obtained having the following physical characteristics:

TLC (developing solvent chloroform:methanol = 20:1): Rf=0.45;

NMR (CDCl$_3$): δ; 4.27−3.83 (2H, multiplet, one of them was D$_2$O exchanged), 3.67 (3H, singlet), 3.65−3.43 (2H, multiplet, one of them was D$_2$O exchanged), 2.68 (1H, double doublet, J=18.0 Hz, J=7.0 Hz) 2.31 (2H, triplet, J=7.0 Hz), 2.20 (1H, double doublet, J=18.0 Hz, J=7.0 Hz), 1.03−0.80(3H, multiplet);

IR (CHCl$_3$): ν; 3400, 1735 cm$^{-1}$;

Mass spectrum: m/e = 379 (M+ − 17), 378 (M+ − 18), 360 (M+ − 36).

EXAMPLE 35

16,16-Propano-ω-homo-PGE$_2$

Proceeding as described in Example 26 using 510 mg. of 9-oxo-11α, 15R-bis-(2-tetrahydropyranyloxy)-16,16-propano-ω-homo-prosta-cis-5,trans-13-dienoic acid, prepared as described in Example 21, 276 mg. (yield 76%) of the title compound were obtained having the following physical characteristics:

TLC (developing solvent chloroform:methanol = 10:1): Rf=0.33;

NMR (CDCl$_3$): δ; 5.77−5.60 (2H, multiplet), 5.60−5.30 (5H, multiplet), 4.15−3.98 (2H, multiplet), 1.48−1.15 (3H, multiplet), 0.89 (3H, broad triplet);

IR (CHCl$_3$): ν; 3400−2400, 1740, 1710, 1160, 1080, 980 cm$^{-1}$;

Mass spectrum: m/e = 389 (M+ − 17), 388 cM+ − 18); 371 (M+ − 35), 370 (M+ − 36).

EXAMPLE 36

16,16-Propano-ω-dihomo-PGE$_2$

Proceeding as described in Example 26 using 313 mg. of 9-oxo-11α, 15R-bis-(2-tetrahydropyranyloxy)-16,16-propano-ω-dihomo-prosta-cis-5, trans-13-dienoic acid, prepared as described in Example 22, 152 mg. (yield 68%) of the title compound were obtained having the following physical characteristics:

TLC (developed twice with solvent chloroform:methanol = 20:1): Rf = 0.20;

NMR (CDCl$_3$): δ; 5.75−5.58 (2H, multiplet), 5.50−5.30 (2H, multiplet), 5.55−5.00 (3H, D$_2$O exchanged), 4.20−3.90 (2H, multiplet), 1.40−1.20 (10H, multiplet), 0.89 (3H, broad triplet);

IR (CHCl$_3$): ν; 3600−2300, 3355, 1740, 1710, 980 cm$^{-1}$;

Mass spectrum: m/e = 402 (M+ − 18), 384 (M+ − 36), 264, 263 (402−139), 246, 245 (384−139), 137, 83, 69, 55;

Optical rotation: [α]$_D^{19}$ = − 54.1° (C = 3.28, CHCl$_3$).

EXAMPLE 37

16,16-Propano-PGE$_2$ methyl ester

A solution of the crude 16,16-propano-PGE$_2$ (100 mg.), prepared as described in Example 26, in methanol (5.0 ml.) was treated with excess diazomethane in diethyl ether. After stirring for a few minutes, the reaction mixture was concentrated. The residue was purified by preparative TLC [three developments using as developing solvent a mixture of chloroform and methanol (20:1) and as eluant a mixture of chloroform and methanol (4:1)] to give 61 mg. (yield 59%) of the pure 16,16-propano-PGE$_2$ methyl ester having the following physical characteristics:

TLC (developing solvent chloroform:methanol = 20:1, three developments): Rf = 0.66;

NMR (CDCl$_3$): δ; 5.74−5.60 (2H, multiplet), 5.50−5.28 (2H, multiplet), 4.11−3.96 (2H, multiplet), 3.66 (3H, singlet), 0.93 (3H, triplet);

IR (CHCl$_3$): ν; 3400, 1745, 980 cm$^{-1}$;

Mass spectrum: m/e = 406 (M+), 388 (M+ − 18), 370 (M+ − 36), 295 (M+ − 111), 277 (M+ − 129).

EXAMPLE 38

16,16-Propano-15-epi-PGE$_2$ methyl ester

Proceeding as described in Example 37 using 16,16-propano-15-epi-PGE$_2$, prepared as described in Example 27, the title compound was obtained as a pale yellow oil having the following physical characteristics:

TLC (developing solvent chloroform:ethanol = 20:1, three developments): Rf = 0.57;

IR (CHCl$_3$): ν; 3450, 1745, 980 cm$^{-1}$.

EXAMPLE 39

16,16-Propano-13,14-dihydro-PGE$_2$ methyl ester

Proceeding as described in Example 37 using 80 mg. of 16,16-propano-13,14-dihydro-PGE$_2$, prepared as described in Example 28, 68 mg. (yield 82%) of the title compound were obtained having the following physical characteristics:

TLC (developing solvent chloroform:methanol = 20:1): Rf=0.49;

NMR: (CDCl$_3$): δ; 5.50−5.30 (2H, multiplet), 4.27−4.00 (1H, multiplet), 3.16 (3H, singlet), 3.61−3.40 (1H, multiplet), 0.92 (3H, broad triplet);

IR (CHCl$_3$): ν; 3400, 1740, 1300−1190, 1160, 1080 cm$^{-1}$.

EXAMPLE 40

16,16-Propano-PGE$_1$ methyl ester

Proceeding as described in Example 37 using 55 mg. of 16,16-propano-PGE$_1$, prepared as described in Example 29, 44 mg. (yield 77%) of the title compound were obtained having the following physical characteristics:

TLC (developing solvent chloroform:methanol = 20:1): Rf=0.55;

IR (CHCl$_3$): ν; 3400, 1740 cm$^{-1}$.

EXAMPLE 41

16,16-Propano-ω-nor-PGE$_2$ methyl ester

Proceeding as described in Example 37 using 120 mg. of 16,16-propano-ω-nor-PGE$_2$, prepared as described in Example 31, 110 mg. (yield 88%) of the title compound were obtained having the following physical characteristics:

TLC (developing solvent chloroform:methanol = 20:1): Rf=0.37;

IR (CHCl$_3$): ν; 3400, 1740, 1300−1200, 1160, 1080, 980 cm$^{-1}$.

EXAMPLE 42

16,16-Propano-ω-nor-13,14-dihydro-PGE$_2$ methyl ester

Proceeding as described in Example 37 using 150 mg. of 16,16-propano-ω-nor-13,14-dihydro-PGE$_2$, prepared as described in Example 32, 130 mg. (yield 83.6%) of the title compound were obtained having the following physical characteristics:

TLC (developing solvent chloroform:methanol = 20:1): Rf=0.31;

NMR (CDCl$_3$): δ; 5.50−5.30 (2H, multiplet), 4.28−4.04 (1H, multiplet), 3.67 (3H, singlet), 3.63−3.47 (1H, multiplet), 1.04−0.83 (3H, multiplet);

IR (CHCl$_3$): ν; 3400, 1740 cm$^{-1}$;

Mass spectrum: m/e = 376 (M$^+$ − 18), 358 (M$^+$ − 36), 345 (M$^+$ − 49), 337 (M$^+$ − 57).

EXAMPLE 43

16,16-Propano-ω-homo-PGE$_2$ methyl ester

Proceeding as described in Example 37 using 181 mg. of 16,16-propano-ω-homo-PGE$_2$, prepared as described in Example 35, 148 mg. (yield 79.1%) of the title compound were obtained having the following physical characteristics:

TLC (developing solvent chloroform:ethanol = 20:1): Rf = 0.23;

NMR (CDCL$_3$): δ; 5.74−5.60 (2H, multiplet), 5.47−5.28 (2H, multiplet), 4.19−3.90 (2H, multiplet), 3.67 (3H, singlet); 1.97−1.16 (8H, multiplet); 0.89 (3H, broad triplet;

IR (CHCl$_3$): ν; 3400, 1740, 1160, 1080, 980 cm$^{-1}$;

Mass spectrum: m/e = 420 (M$^+$), 402 (M$^+$ − 18), 384 (M$^+$ − 36).

EXAMPLE 44

16,16-Propano-ω-dihomo-PGE$_2$ methyl ester

Proceeding as described in Example 37 using 96 mg. of 16,16-propano-ω-dihomo-PGE$_2$, prepared as described in Example 36, 81 mg. (yield 81%) of the title compound were obtained having the following physical characteristics:

TLC (developing solvent chloroform:methanol = 20:1): Rf = 0.21;

NMR (CDCl$_3$): δ; 5.90−5.50 (2H, multiplet), 5.50−5.16 (2H, multiplet), 4.03 (1H, broad doublet, J = 7.0 Hz), 4.20−3.90 (1H, multiplet), 3.67 (3H, singlet), 2.75 (1H, double doublet, J = 18.0 Hz, J = 7.0 Hz), 1.45−1.15 (10H, multiplet), 0.89 (3H, broad triplet;

IR (CHCl$_3$): ν; 3400, 1740, 980 cm$^{-1}$;

Mass spectrum: m/e = 416 (M$^+$ − 18), 398 (M$^+$ − 36), 385 (416−OMe), 367 (398−OMe), 295 (M$^+$ − 139), 277 (416−139), 137, 83, 81, 69, 55, 41;

Optical rotation: [α]$_D^{19}$ = − 67.2° (C = 2.85 CHCl$_3$).

EXAMPLE 45

16,16-Propano-15-epi-PGA$_2$

A solution of 183 mg. of 16,16-propano-15-epi-PGE$_2$, prepared as described in Example 27, in THF (10 ml.) was treated with 1N hydrochloric acid (10 ml.) and stirred for 3.5 hours at 57° C. The reaction mixture was diluted with 50 ml. of water, extracted with methylene chloride, dried over sodium sulphate and concentrated to yield 179 mg. of oily product. The product was purified by preparative TLC [using as developing solvent a mixture of chloroform and ethanol (50:1) for two developments and a mixture of chloroform and ethanol (20:1) for three developments, and a mixture of chloroform and methanol (4:1) as eluant] to give 79 mg. (yield 45%) of pure 16,16-propano 15-epi-PGA$_2$ having the following physical characteristics:

TLC (developing solvent chloroform:ethanol = 40:1, three developments): Rf = 0.59;

NMR (CDCl$_3$): δ; 7.48 (1H, double doublet, J = 5.5 Hz, J = 2.0 Hz), 6.19 (1H, double doublet, J = 5.5 Hz, J = 1.8 Hz), 6.20−5.75 (2H, D$_2$O exchanged), 5.73−5.57 (2H, multiplet), 5.52−5.34 (2H, multiplet), 4.10−3.97 (1H, multiplet), 3.35−3.17 (1H, multiplet), 0.92 (3H, triplet);

IR (CHCl$_3$): ν; 3700−2300, 3400, 1710, 1600, 980 cm$^{-1}$;

Mass spectrum: m/e = 374 (M$^+$), 356 (M$^+$ − 18), 264 (M$^+$ − 110), 246 (M$^+$ − 128);

UV: λ$_{max}^{MeOH}$ 217 mμ (ε 6,300);

Optical rotation: [α]$_D^{25}$ = + 95.5° (C = 1.42, CHCl$_3$).

In a similar manner to that described in Example 45 there may be prepared 16,17-ethano-16-phenyl-ω-trinor-PGA$_2$, 16,18-methano-18-methyl-ω-nor-PGA$_2$, 16,17-ethano-ω-dinor-PGA$_2$ and 16,18-methano-ω-dihomo-PGA$_2$.

The present invention includes within its scope pharmaceutical compositions which comprise at least one prostaglandin analogue of general formula VII or a cyclodextrin clathrate thereof or, when R represents a hydrogen atom, a non-toxic salt thereof, or a prostaglandin alcohol of general formula XXX or a cyclodextrin clathrate thereof, together with a pharmaceutical carrier or coating. In clinical practice the new compounds of the present invention will normally be administered orally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses are generally between 0.05 and 50 μg./kg. body weight by oral administration in the treatment of gastric ulceration, between 0.1 and 50 μg./kg. body weight by aerosol administration in the treatment of asthma, between 0.01 and 5 mg./kg. body weight by oral administration in the treatment of disorders of the peripheral circulation and between 0.01 and 5 mg./kg. body weight by oral administration in the prevention and treatment of cerebral thrombosis and myocardial infarction.

Prostaglandin compounds according to the present invention may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 0.001 to 5 mg., and preferably 0.01 to 0.5 mg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 0.01 to 0.5 mg., of active ingredient per ml. of solution or suspension. It is important that the pH of solutions and suspensions used, according to the present invention, to generate aerosols should be kept within the range 3 to 8 and preferable that they should be stored at or below 4° C.; to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Examples illustrate pharmaceutical compositions according to the invention.

EXAMPLE 46

16,16-Propano-PGE$_2$ (200 μg.) was dissolved in ethanol (1 ml.) and the solution obtained was added to an aqueous solution (12 ml.) containing sodium carbonate (50 mg.). Aqueous sodium chloride solution (0.9% w/v, 2 ml.) was then added to give a final volume of 15 ml. The solution was then sterilized by passage through a bacteria-retaining filter and placed in 1.5 ml. portions in 5 ml. ampoules, to give 20 μg. of 16,16-propano-PGE$_2$ (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

The prostaglandin analogues of the present invention are especially useful for the treatment of gastric ulceration without causing, as an undesired side-effect, a hypotensive action.

EXAMPLE 47

16,16-Propano-PGE$_2$ (5.0 mg.) was dissolved in ethanol (10 ml.) and the solution mixed with mannitol (18.5 g.). The mixture was sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 50 μg. of 16,16-propano-PGE$_2$, which after swallowing of the capsules is released into the stomach.

What we claim is:

1. A compound of the formula:

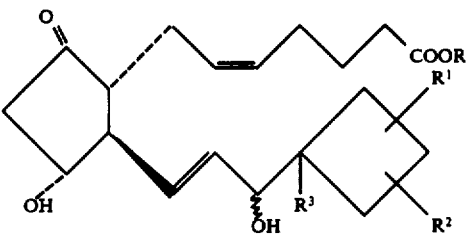

wherein R represents a hydrogen atom or methyl group, R$^1$ and R$^2$ represent hydrogen atoms and R$^3$ represents an alkyl group containing from 1-6 carbon atoms, the non-toxic salts thereof when R is hydrogen, the C$_1$ to C$_{12}$ alkyl esters thereof, and the cyclodextrin clathrates thereof.

2. A compound according to claim 1 wherein R represents a methyl group.

3. A compound according to claim 1, wherein the hydroxy radical attached to the carbon atom in the 15-position of the general formula depicted in claim 1 is in α-configuration.

4. A compound according to claim 1 which is 16,16-propano-PGE$_2$ and its methyl ester.

5. A compound according to claim 1 which is 16,16-propano-15-epi-PGE$_2$.

6. A compound according to claim 1 which is 16,16-propano-ω-nor-PGE$_2$.

7. A compound according to claim 1 which is 16,16-propano-ω-homo-PGE$_2$.

8. A compound according to claim 1 which is 16,16-propano-ω-dihomo-PGE$_2$.

9. 16,17-ethano-16-phenyl-ω-trinor-PGE$_2$.

* * * * *